(12) United States Patent
Fraser et al.

(10) Patent No.: US 6,608,025 B1
(45) Date of Patent: Aug. 19, 2003

(54) HUMAN NESP55 POLYPEPTIDES, POLYNUCLEOTIDES AND USES THEREOF

(75) Inventors: Douglas Fraser, Nottingham (GB); Steven St. Gallay, Nottingham (GB)

(73) Assignee: Knoll, AG, Ludwigshafen (DE)

( * ) Notice: Subject to any disclaimer, the term of this patent is extended or adjusted under 35 U.S.C. 154(b) by 0 days.

(21) Appl. No.: 09/468,554

(22) Filed: Dec. 21, 1999

Related U.S. Application Data

(63) Continuation-in-part of application No. 09/444,648, filed on Nov. 22, 1999.

(30) Foreign Application Priority Data

Jul. 23, 1999 (GB) ............................................. 9917165

(51) Int. Cl.[7] ........................ A61K 38/07; A61K 38/08; C07K 5/103; C07K 7/06; C07K 14/47
(52) U.S. Cl. .............................. 514/2; 514/16; 514/18; 530/300; 530/328; 530/330; 530/350
(58) Field of Search ................................ 530/300, 350, 530/330, 328; 514/18, 16, 2

(56) References Cited

PUBLICATIONS

Christie, D.L. et al. "Identification of kex2–related proteases in chromaffin granules by partial amino acid sequence analysis" *J. Biol. Chem.* 266(24):15679–15683 (Aug. 25, 1991).

Egger, C. et al. "Different degrees of processing of secretogranin II in large dense core vesicles of bovine adrenal medulla and sympathetic axons correlate with their content of soluble PC1 and PC2" *Neurosci. Lett.* 159:199–201 (Sep. 3, 1993).

Fuller, R.S. et al. "Intracellular targeting and structural conservation of a prohormone–processing endoprotease" *Science* 246(4929):482–6 (Oct. 27, 1989).

Hamblin, M.W. et al. "Primary structure and functional characterization of a human 5–HT$_{1D}$–type serotonin receptor" *Mol Pharmacol* 40(2):143–148 (1991).

Hayward, B.E. et al., "Bidirectional imprinting of a single gene: GNAS1 encodes maternally, paternally, and biallelically derived proteins" *Proc. Natl. Acad. Sci. USA* 95:15475–15480 (Dec. 1998).

Ischia, R. et al. "Molecular cloning and characterization of NESP55, a novel chromogranin–like precursor of a peptide with 5–HT$_{1B}$ receptor antagonist activity" *J Biol Chem* 272(17):11657–11662 (Apr. 25, 1997).

Jin, H. et al. "Characterization of the human 5–hydroxytryptamine$_{1B}$ receptor" *J. Biol. Chem.* 267(9):5735–5738 (Mar. 25, 1992).

Kirchmair, R. et al. "Differential subcellular distribution of PC1, PC2 and furin in bovine adrenal medulla and secretion of PC1 and PC2 from this tissue" *Neurosci Lett* 143(1–2):143–145 (Aug. 31, 1992).

Levy, F.O. et al. "Molecular cloning of a human serotonin receptor (S12) with a pharmacological profile resembling that of the 5–HT$_{1D}$ subtype" *J. Biol. Chem.* 267(11):7553–7562 (Apr. 15, 1992).

Lovisetti–Scamihorn, P. et al. "Pig splenic nerve: peptides derived from chromogranins by proteolytic processing during axonal transport" *Regul Pept* 79(1):63–67 (Jan. 1, 1999).

Lovisetti–Scamihorn, P. et al. "Relative amounts and molecular forms of NESP55 in various bovine tissues" *Brain Res* 829(1–2):99–106 (May 22, 1999).

Sigafoos, J. et al. "Novel peptides from adrenomedullary chromaffin vesicles" *J. Anat.* 183:253–264 (1993).

Wise, R.J. et al. "expression of a human proprotein processing enzyme: Correct cleavage of the von Willebrand factor precursor at a paired basic amino acid site" *Proc. Natl. Acad. Sci. USA* 87:9378–9382 (Dec. 1990).

*Primary Examiner*—Gary Kunz
*Assistant Examiner*—Stephen Gucker
(74) *Attorney, Agent, or Firm*—Lahive & Cockfield, LLP; Guilio A. DeConti, Jr., Esq.; Elizabeth A. Hanley, Esq.

(57) ABSTRACT

A substantially pure polypeptide (human NESP55) comprising the amino acid sequence

```
                                          (SEQ ID NO: 2)
IRLEVPKRMDRRSRAQQWRRARHNYNDLCPPIGRRAATALLWLSCSIALL

RALATSNARAQQRAAAQQRRSFLNAHHRSGAQVFPESPESESDHEHEEAD

LELSLPECLEYEEEFDYETESETESEIESETDFETEPETAPTTEPETEPE

DDRGPVVPKHSTFGQSLTQRLHALKLRSPDASPSRAPPSTQEPQSPREGE

ELKPEDKDPRRDPEESKEPKEEKQRRRCKPKKPTRRDASPESPSKKGPIP

IRRH
``` or a variant, fragment, fusion or derivative thereof, or a fusion of a said variant or fragment or derivative, wherein the polypeptide variant has an amino acid sequence which has at least 90% identity with the amino acid sequence given above.

NESP55 or fragments thereof may be useful in medicine for the treatment of obesity.

6 Claims, 2 Drawing Sheets

SEQUENCE LISTING

<160> NUMBER OF SEQ ID NOS: 16

<210> SEQ ID NO 1
<211> LENGTH: 2235
<212> TYPE: DNA
<213> ORGANISM: Homo sapiens
<220> FEATURE:
<221> NAME/KEY: CDS
<222> LOCATION: (3)...(761)

<400> SEQUENCE: 1

```
ga att cgg ctc gag gtg cct aag agg atg gat cgg agg tcc cgg gct        47
   Ile Arg Leu Glu Val Pro Lys Arg Met Asp Arg Arg Ser Arg Ala
   1               5                  10                  15 cag cag tgg cgc cga gct cgc cat aat tac aac gac ctg tgc ccg ccc        95
Gln Gln Trp Arg Arg Ala Arg His Asn Tyr Asn Asp Leu Cys Pro Pro
                20                  25                  30 ata ggc cgc cgg gca gcc acc gcg ctc ctc tgg ctc tcc tgc tcc atc       143
Ile Gly Arg Arg Ala Ala Thr Ala Leu Leu Trp Leu Ser Cys Ser Ile
            35                  40                  45 gcg ctc ctc cgc gcc ctt gcc acc tcc aac gcc cgt gcc cag cag cgc       191
Ala Leu Leu Arg Ala Leu Ala Thr Ser Asn Ala Arg Ala Gln Gln Arg
        50                  55                  60 gcg gct gcc caa cag cgc cgg agc ttc ctt aac gcc cac cac cgc tcc       239
Ala Ala Ala Gln Gln Arg Arg Ser Phe Leu Asn Ala His His Arg Ser
    65                  70                  75 ggc gcc cag gta ttc cct gag tcc ccc gaa tcg gaa tct gac cac gag       287
Gly Ala Gln Val Phe Pro Glu Ser Pro Glu Ser Glu Ser Asp His Glu
 80                  85                  90                  95 cac gag gag gca gac ctt gag ctg tcc ctc ccc gag tgc cta gag tac       335
His Glu Glu Ala Asp Leu Glu Leu Ser Leu Pro Glu Cys Leu Glu Tyr
                100                 105                 110 gag gaa gag ttc gac tac gag acc gag agc gag acc gag tcc gaa atc       383
Glu Glu Glu Phe Asp Tyr Glu Thr Glu Ser Glu Thr Glu Ser Glu Ile
            115                 120                 125 gag tcc gag acc gac ttc gag acc gag cct gag acc gcc ccc acc act       431
Glu Ser Glu Thr Asp Phe Glu Thr Glu Pro Glu Thr Ala Pro Thr Thr
        130                 135                 140 gag ccc gag acc gag cct gaa gac gat cgc ggc ccg gtg gtg ccc aag       479
Glu Pro Glu Thr Glu Pro Glu Asp Asp Arg Gly Pro Val Val Pro Lys
    145                 150                 155 cac tcc acc ttc ggc cag tcc ctc acc cag cgt ctg cac gct ctc aag       527
His Ser Thr Phe Gly Gln Ser Leu Thr Gln Arg Leu His Ala Leu Lys
160                 165                 170                 175 ttg cga agc ccc gac gcc tcc cca agt cgc gcg ccg ccc agc act cag       575
Leu Arg Ser Pro Asp Ala Ser Pro Ser Arg Ala Pro Pro Ser Thr Gln
                180                 185                 190 gag ccc cag agc ccc agg gaa ggg gag gag ctc aag ccc gag gac aaa       623
Glu Pro Gln Ser Pro Arg Glu Gly Glu Glu Leu Lys Pro Glu Asp Lys
            195                 200                 205 gat cca agg gac ccc gaa gag tcg aag gag ccc aag gag gag aag cag       671
Asp Pro Arg Asp Pro Glu Glu Ser Lys Glu Pro Lys Glu Glu Lys Gln
        210                 215                 220 cgg cgt cgc tgc aag cca aag aag ccc acc cgc gtt gac gcg tcc ccg       719
Arg Arg Arg Cys Lys Pro Lys Lys Pro Thr Arg Arg Asp Ala Ser Pro
    225                 230                 235 gag tcc cct tcc aaa aag gga ccc atc ccc atc cgg cgt cac                761
Glu Ser Pro Ser Lys Lys Gly Pro Ile Pro Ile Arg Arg His
240                 245                 250
```

-continued

```
taatggagga cgccgtccag attctccttg ttttcatgga ttcaggtgct ggagaatctg    821
gtaaaagcac cattgtgaag cagatgagga tcctgcatgt taatgggttt aatggagagg    881
gcggcgaaga ggacccgcag gctgcaagga gcaacagcga tggtgagaag caaccaaag    941 tgcaggacat caaaaacaac ctgaaagagg cgattgaaac cattgtggcc gccatgagca   1001
acctggtgcc ccccgtggag ctggccaacc ccgagaacca gttcagagtg gactacattc   1061
tgagtgtgat gaacgtgcct gactttgact tccctcccga attctatgag catgccaagg   1121
ctctgtggga ggatgaagga gtgcgtgcct gctacgaacg ctccaacgag taccagctga   1181
ttgactgtgc ccagtacttc ctggacaaga tcgacgtgat caagcaggct gactatgtgc   1241
cgagcgatca ggacctgctt cgctgccgtg tcctgacttc tggaatcttt gagaccaagt   1301
tccaggtgga caaagtcaac ttccacatgt ttgacgtggg tggccagcgc gatgaacgcc   1361
gcaagtggat ccagtgcttc aacgatgtga ctgccatcat cttcgtggtg ccagcagca   1421 gctacaacat ggtcatccgg gaggacaacc agaccaaccg cctgcaggag gctctgaacc   1481
tcttcaagag catctggaac aacagatggc tgcgcaccat ctctgtgatc ctgttcctca   1541
acaagcaaga tctgctcgct gagaaagtcc ttgctgggaa atcgaagatt gaggactact   1601
ttccagaatt tgctcgctac actactcctg aggatgctac tcccgagccc ggagaggacc   1661
cacgcgtgac ccgggccaag tacttcattc gagatgagtt tctgaggatc agcactgcca   1721
gtggagatgg gcgtcactac tgctaccctc atttcacctg cgctgtggac actgagaaca   1781
tccgccgtgt gttcaacgac tgccgtgaca tcattcagcg catgcacctt cgtcagtacg   1841
agctgctcta agaagggaac ccccaaattt aattaaagcc ttaagcacaa ttaattaaaa   1901
gtgaaacgta attgtacaag cagttaatca cccaccatag ggcatgatta acaaagcaac   1961
cttttccttc ccccgagtga ttttgcgaaa ccccctttc ccttcagctt gcttagatgt    2021
tccaaattta gaaagcttaa ggcggcctac agaaaaagga aaaaggcca caaagttcc    2081 ctctcacttt cagtaaaaat aaataaaaca gcagcagcaa acaaataaaa tgaaataaaa   2141
gaaacaaatg aaataaatat tgtgttgtgc agcattaaaa aaaatcaaaa taaaattaa    2201 atgtgagcaa aaaaaaaaaa aaaagggcgg ccgc                               2235
```

<210> SEQ ID NO 2
<211> LENGTH: 253
<212> TYPE: PRT
<213> ORGANISM: Homo sapiens

<400> SEQUENCE: 2

```
Ile Arg Leu Glu Val Pro Lys Arg Met Asp Arg Arg Ser Arg Ala Gln
 1               5                  10                  15

Gln Trp Arg Arg Ala Arg His Asn Tyr Asn Asp Leu Cys Pro Pro Ile
            20                  25                  30

Gly Arg Arg Ala Ala Thr Ala Leu Leu Trp Leu Ser Cys Ser Ile Ala
        35                  40                  45

Leu Leu Arg Ala Leu Ala Thr Ser Asn Ala Arg Ala Gln Gln Arg Ala
    50                  55                  60

Ala Ala Gln Gln Arg Arg Ser Phe Leu Asn Ala His His Arg Ser Gly
65                  70                  75                  80

Ala Gln Val Phe Pro Glu Ser Pro Glu Ser Glu Ser Asp His Glu His
                85                  90                  95

Glu Glu Ala Asp Leu Glu Leu Ser Leu Pro Glu Cys Leu Glu Tyr Glu
            100                 105                 110
```

```
Glu Glu Phe Asp Tyr Glu Thr Glu Ser Glu Thr Glu Ser Glu Ile Glu
            115                 120                 125

Ser Glu Thr Asp Phe Glu Thr Glu Pro Glu Thr Ala Pro Thr Thr Glu
        130                 135                 140

Pro Glu Thr Glu Pro Glu Asp Asp Arg Gly Pro Val Val Pro Lys His
145                 150                 155                 160

Ser Thr Phe Gly Gln Ser Leu Thr Gln Arg Leu His Ala Leu Lys Leu
                165                 170                 175

Arg Ser Pro Asp Ala Ser Pro Ser Arg Ala Pro Pro Ser Thr Gln Glu
                180                 185                 190

Pro Gln Ser Pro Arg Glu Gly Glu Glu Leu Lys Pro Glu Asp Lys Asp
            195                 200                 205

Pro Arg Asp Pro Glu Glu Ser Lys Glu Pro Lys Glu Glu Lys Gln Arg
        210                 215                 220

Arg Arg Cys Lys Pro Lys Lys Pro Thr Arg Arg Asp Ala Ser Pro Glu
225                 230                 235                 240

Ser Pro Ser Lys Lys Gly Pro Ile Pro Ile Arg Arg His
                245                 250
```

```
<210> SEQ ID NO 3
<211> LENGTH: 4
<212> TYPE: PRT
<213> ORGANISM: Bovine Sp.

<400> SEQUENCE: 3

Leu Ser Ala Leu
 1

<210> SEQ ID NO 4
<211> LENGTH: 7
<212> TYPE: PRT
<213> ORGANISM: Bovine Sp.

<400> SEQUENCE: 4

Ala Ile Pro Ile Arg Arg His
 1               5

<210> SEQ ID NO 5
<211> LENGTH: 4
<212> TYPE: PRT
<213> ORGANISM: Homo sapiens

<400> SEQUENCE: 5

Leu His Ala Leu
 1

<210> SEQ ID NO 6
<211> LENGTH: 8
<212> TYPE: PRT
<213> ORGANISM: Homo sapiens

<400> SEQUENCE: 6

Gly Pro Ile Pro Ile Arg Arg His
 1               5

<210> SEQ ID NO 7
<211> LENGTH: 4
<212> TYPE: PRT
<213> ORGANISM: Homo sapiens

<400> SEQUENCE: 7
```

```
Ser Phe Leu Asn
  1

<210> SEQ ID NO 8
<211> LENGTH: 4
<212> TYPE: PRT
<213> ORGANISM: Homo sapiens

<400> SEQUENCE: 8

Pro Ser Lys Lys
  1

<210> SEQ ID NO 9
<211> LENGTH: 4
<212> TYPE: PRT
<213> ORGANISM: Homo sapiens

<400> SEQUENCE: 9

Met Asp Arg Arg
  1

<210> SEQ ID NO 10
<211> LENGTH: 4
<212> TYPE: PRT
<213> ORGANISM: Homo sapiens

<400> SEQUENCE: 10

Ala Thr Ala Leu
  1

<210> SEQ ID NO 11
<211> LENGTH: 64
<212> TYPE: PRT
<213> ORGANISM: Homo sapiens
<220> FEATURE:
<221> NAME/KEY: VARIANT
<222> LOCATION: 1, 2, 3, 4, 5, 6, 7, 8, 9, 10, 11, 12, 13, 14, 15, 16,
      17, 18, 19, 20, 21, 22, 23, 24, 25, 26, 27, 28, 29, 30, 35, 36,
      37, 38, 39, 40, 41, 42, 43, 44, 45, 46, 47, 48, 49, 50, 51, 52,
      53, 54, 55, 56, 57, 58, 59, 60, 61, 62, 63, 64
<223> OTHER INFORMATION: Xaa = Any Amino Acid
<220> FEATURE:
<221> NAME/KEY: VARIANT
<222> LOCATION: 1, 2, 3, 4, 5, 6, 7, 8, 9, 10, 11, 12, 13, 14, 15, 16,
      17, 18, 19, 20, 21, 22, 23, 24, 25, 26, 27, 28, 29, 30, 35, 36,
      37, 38, 39, 40, 41, 42, 43, 44, 45, 46, 47, 48, 49, 50, 51, 52,
      53, 54, 55, 56, 57, 58, 59, 60, 61, 62, 63, 64
<223> OTHER INFORMATION: Xaa = Any Amino Acid

<400> SEQUENCE: 11

Xaa Xaa Xaa Xaa Xaa Xaa Xaa Xaa Xaa Xaa Xaa Xaa Xaa Xaa Xaa Xaa
  1               5                  10                  15

Xaa Xaa Xaa Xaa Xaa Xaa Xaa Xaa Xaa Xaa Xaa Xaa Xaa Xaa Leu His
             20                  25                  30

Ala Leu Xaa Xaa Xaa Xaa Xaa Xaa Xaa Xaa Xaa Xaa Xaa Xaa Xaa Xaa
             35                  40                  45

Xaa Xaa Xaa Xaa Xaa Xaa Xaa Xaa Xaa Xaa Xaa Xaa Xaa Xaa Xaa Xaa
         50                  55                  60

<210> SEQ ID NO 12
<211> LENGTH: 68
<212> TYPE: PRT
<213> ORGANISM: Homo sapiens
<220> FEATURE:
<221> NAME/KEY: VARIANT
<222> LOCATION: 1, 2, 3, 4, 5, 6, 7, 8, 9, 10, 11, 12, 13, 14, 15, 16,
      17, 18, 19, 20, 21, 22, 23, 24, 25, 26, 27, 28, 29, 30, 39, 40,
```

```
        41, 42, 43, 44, 45, 46, 47, 48, 49, 50, 51, 52, 53, 54, 55, 56,
        57, 58, 59, 60, 61, 62, 63, 64, 65, 66, 67, 68
<223> OTHER INFORMATION: Xaa = Any Amino Acid
<220> FEATURE:
<221> NAME/KEY: VARIANT
<222> LOCATION: 1, 2, 3, 4, 5, 6, 7, 8, 9, 10, 11, 12, 13, 14, 15, 16,
        17, 18, 19, 20, 21, 22, 23, 24, 25, 26, 27, 28, 29, 30, 39, 40,
        41, 42, 43, 44, 45, 46, 47, 48, 49, 50, 51, 52, 53, 54, 55, 56,
        57, 58, 59, 60, 61, 62, 63, 64, 65, 66, 67, 68
<223> OTHER INFORMATION: Xaa = Any Amino Acid

<400> SEQUENCE: 12

Xaa Xaa Xaa Xaa Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Gly Pro
            20                  25                  30

Ile Pro Ile Arg Arg His Xaa Xaa Xaa Xaa Xaa Xaa Xaa Xaa Xaa
            35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa
65

<210> SEQ ID NO 13
<211> LENGTH: 11
<212> TYPE: PRT
<213> ORGANISM: Homo sapiens

<400> SEQUENCE: 13

Gln Arg Leu His Ala Leu Lys Leu Arg Ser Pro
 1               5                  10

<210> SEQ ID NO 14
<211> LENGTH: 11
<212> TYPE: PRT
<213> ORGANISM: Bovine Sp.

<400> SEQUENCE: 14

Glu Arg Leu Ser Ala Leu Arg Leu Arg Ser Pro
 1               5                  10

<210> SEQ ID NO 15
<211> LENGTH: 241
<212> TYPE: PRT
<213> ORGANISM: Bos taurus

<400> SEQUENCE: 15

Met Asp Arg Arg Ser Arg Pro Gln Leu Gly Arg Arg Ala Arg His Asn
 1               5                  10                  15

Tyr Asn Asp Leu Cys Pro Pro Ile Gly Arg Arg Ala Ala Thr Ala Leu
            20                  25                  30

Leu Trp Leu Ser Cys Ser Ile Ala Leu Leu Arg Ala Leu Ala Thr Ser
        35                  40                  45

Ser Thr Arg Ala Gln Gln Arg Ala Ala Gln Arg Thr Phe Leu
    50                  55                  60

Asn Ala His His Arg Ser Ala Ala Gln Val Phe Pro Glu Pro Pro Glu
65                  70                  75                  80

Ser Asp His Glu Asp Thr Asp Phe Glu Pro Ser Leu Pro Glu Cys Pro
                85                  90                  95

Glu Tyr Gln Glu Glu Glu Phe Asp Tyr Glu Ser Glu Thr Glu Ser Glu
               100                 105                 110
```

```
Ser Glu Ile Glu Ser Glu Thr Glu Phe Glu Thr Glu Ser Asp Thr Ala
            115                 120                 125

Pro Thr Thr Glu Pro Glu Thr Glu Pro Glu Asp Glu Pro Gly Pro Val
    130                 135                 140

Val Pro Lys Arg Pro Thr Phe His Gln Ser Leu Thr Glu Arg Leu Ser
145                 150                 155                 160

Ala Leu Arg Leu Arg Ser Pro Asp Ala Ser Pro Ser Arg Ala Pro Pro
                165                 170                 175

Ser Thr Gln Glu Ser Glu Ser Pro Arg Gln Gly Glu Glu Pro Glu Asp
            180                 185                 190

Lys Asp Pro Arg Asp Pro Glu Glu Ser Glu Glu Pro Lys Glu Glu Glu
            195                 200                 205

Lys Gln Gln His Arg Cys Lys Pro Lys Lys Pro Thr Arg Arg Asp
    210                 215                 220

Pro Ser Pro Glu Ser Pro Ser Lys Arg Gly Ala Ile Pro Ile Arg Arg
225                 230                 235                 240

His

<210> SEQ ID NO 16
<211> LENGTH: 256
<212> TYPE: PRT
<213> ORGANISM: Artificial Sequence
<220> FEATURE:
<223> OTHER INFORMATION: consensus sequence
<220> FEATURE:
<221> NAME/KEY: VARIANT
<222> LOCATION: 1, 2, 3, 4, 5, 6, 7, 8, 15, 17, 18, 57, 58, 68, 71, 80,
      87, 91, 92, 93, 94, 95, 98, 99, 101, 103, 109, 112, 120, 122, 124,
      133, 138, 139, 153, 154, 161, 162, 165, 173, 176, 194, 202, 203,
      204, 217, 223, 224, 225, 227, 228, 240, 248
<223> OTHER INFORMATION: Xaa = Any Amino Acid
<220> FEATURE:
<221> NAME/KEY: VARIANT
<222> LOCATION: 250
<223> OTHER INFORMATION: Xaa = Any Amino Acid

<400> SEQUENCE: 16

Xaa Xaa Xaa Xaa Xaa Xaa Xaa Xaa Met Asp Arg Ser Arg Xaa Gln
1               5                   10                  15

Xaa Xaa Arg Arg Ala Arg His Asn Tyr Asn Asp Leu Cys Pro Pro Ile
        20                  25                  30

Gly Arg Arg Ala Ala Thr Ala Leu Leu Trp Leu Ser Cys Ser Ile Ala
            35                  40                  45

Leu Leu Arg Ala Leu Ala Thr Ser Xaa Xaa Arg Ala Gln Gln Arg Ala
    50                  55                  60

Ala Ala Gln Xaa Arg Arg Xaa Phe Leu Asn Ala His His Arg Ser Xaa
65                  70                  75                  80

Ala Gln Val Phe Pro Glu Xaa Pro Glu Ser Xaa Xaa Xaa Xaa Xaa His
            85                  90                  95

Glu Xaa Xaa Asp Xaa Glu Xaa Ser Leu Pro Glu Cys Xaa Glu Tyr Xaa
            100                 105                 110

Glu Glu Glu Phe Asp Tyr Glu Xaa Glu Xaa Glu Xaa Glu Ser Glu Ile
            115                 120                 125

Glu Ser Glu Thr Xaa Phe Glu Thr Glu Xaa Xaa Thr Ala Pro Thr Thr
            130                 135                 140

Glu Pro Glu Thr Glu Pro Glu Asp Xaa Xaa Gly Pro Val Val Pro Lys
145                 150                 155                 160

Xaa Xaa Thr Phe Xaa Gln Ser Leu Thr Glx Arg Leu Xaa Ala Leu Xaa
            165                 170                 175
```

-continued

```
Leu Arg Ser Pro Asp Ala Ser Pro Ser Arg Ala Pro Pro Ser Thr Gln
            180                 185                 190

Glu Xaa Glx Ser Pro Arg Glx Gly Glu Xaa Xaa Xaa Pro Glu Asp Lys
        195                 200                 205

Asp Pro Arg Asp Pro Glu Glu Ser Xaa Glu Pro Lys Glu Glu Xaa Xaa
        210                 215                 220

Xaa Gln Xaa Xaa Arg Cys Lys Pro Lys Lys Pro Thr Arg Arg Asp Xaa
225                 230                 235                 240

Ser Pro Glu Ser Pro Ser Lys Xaa Gly Xaa Ile Pro Ile Arg Arg His
                245                 250                 255
```

HUMAN NESP55 POLYPEPTIDES, POLYNUCLEOTIDES AND USES THEREOF

RELATED APPLICATIONS

This application is a continuation-in-part of U.S. Ser. No. 09/444,648, filed Nov. 22, 1999, abandoned, the entire contents of which are hereby incorporated by reference.

FIELD OF THE INVENTION

The present invention relates to polypeptides, polynucleotides and uses thereof in screening and in medicine.

BACKGROUND OF THE INVENTION

Obesity is a serious health hazard that may be accompanied by elevated levels of blood cholesterol and elevated blood pressure. There is an increased risk of mortality from coronary heart disease, stroke, certain cancers and non-insulin dependent diabetes, as well as an association with several non-fatal health problems.

Obesity is usually measured by Body Mass Index (BMI), which is obtained from a simple formula, given by:

$$BMI=(\text{mass/kg}) \times (\text{height/m})^{-2}$$

BMI values in adults have been categorised according to the severity of health risk, with the higher graded numbers associated with a more severe risk (Table 1). Modified versions of this scale have been derived which account for gender, and there are other considerations such as age and body frame (see, for example Black's Medical Dictionary).

TABLE 1

| Grade | BMI | Category |
| --- | --- | --- |
| 3 | >40 | Severely obese |
| 2 | 30–40 | Obese |
| 1 | 25–29.9 | Overweight |
| 0 | 20–24.9 | Desirable weight |
| Ungraded | <20 | Underweight |

Desirable body weights for adults according to gender, height and build are given in Appendix 6C of Black's Medical Dictionary.

Ischia et al (1997) *J Biol Chem* 272, 11657–11662 describes the cloning of a bovine chromogranin-like polypeptide termed NESP55 (neuroendocrine secretory protein of Mol Wt 55,000). A partial sequence for mouse NESP55 is also presented. As reviewed by Ischia et al, chromogranins are proteins found in the content of large dense core vesicles, specialised vesicular containers found in presynaptic terminals which store neurotransmitters and peptides prior to exocytic release during synaptic transmission. Chromogranins have an acid pI of 4 to 5 and typically consist of 200–700 amino acids with glutamic acid as the most abundant individual amino acid. Multiple pairs of consecutive basic amino acid residues, known as potential cleavage sites for trypsin-like endoproteases, are present. Both intracellular (involvement in sorting of peptidergic components to the large dense core vesicles) as well as extracellular functions (representing precursors of small biologically active neuropeptides such as pancreastatin, vasostatin or secretoneurin) have been proposed for chromogranins.

Bovine NESP55 is proposed to be a precursor for the tetrapeptide Leu-Ser-Ala-Leu (SEQ ID NO: 3), which has been identified as an endogenous antagonist of the serotonergic 5-HT$_{1B}$ receptor subtype. The serotonergic system is thought to play a role in mental disorders, particularly depression. A second amino acid sequence, GAIPIRRH (SEQ ID NO: 4), present at the C-terminus of bovine NESP55 is the same as that of a peptide identified in the secretory content of chromaffin granules (Sigafoos et al (1993) *J Anat* 183, 253–264). A function was not assigned to this peptide, and there has been no suggestion that either peptide is involved in obesity.

SUMMARY OF THE INVENTION

We have identified a human homologue of the bovine NESP55 gene. Further, we have found that NESP55 is, at least in humans, linked with obesity. Accordingly, the invention provides isolated human neuroendocrine secretory protein 55 (NESP55).

In one aspect, the invention provides a substantially pure polypeptide comprising the amino acid sequence of SEQ ID NO: 2 or a variant, fragment, fusion or derivative thereof, or a fusion of a said variant or fragment or derivative, wherein the polypeptide variant has an amino acid sequence which has at least 90% identity with the amino acid sequence of SEQ ID NO: 2. The invention also provides a processed polypeptide derivable from human NESP55 wherein the processed polypeptide is derivable, or predicted from the amino acid sequence of human NESP55 to be derivable, by endoproteolytic cleavage of human NESP55. In one embodiment, the N-terminal amino acid residue of the processed polypeptide is immediately preceded in the amino acid sequence of human NESP55 by two consecutive basic amino acid residues or by a basic amino acid residue. In another embodiment, the C-terminus of the processed polypeptide is immediately preceded by two consecutive basic amino acid residues or by a basic amino acid residue. In preferred embodiments, the processed polypeptide comprises the amino acid sequence LHAL (SEQ ID NO: 5) or the amino acid sequence GPIPIRRH (SEQ ID NO: 6), or consists of the amino acid sequence LHAL (SEQ ID NO: 5) or the amino acid sequence GPIPIRRH (SEQ ID NO: 6).

The invention also provides a polypeptide consisting of the amino acid sequence X$_n$LHALZ$_m$ (SEQ ID NO: 11), or X$_n$GPIPIRRHZ$_m$ (SEQ ID NO: 12) wherein X$_n$ represents the amino acid sequence of the consecutive n amino acids immediately N terminal to the amino acid sequence LHAL (SEQ ID NO: 5) or GPIPIRRH (SEQ ID NO: 6) and wherein Z$_m$ represents the amino acid sequence of the consecutive m amino acids immediately C terminal to the amino acid sequence LHAL (SEQ ID NO: 5) or GPIPIRRH (SEQ ID NO: 6), wherein n and m may independently be any number between 0 and 30 amino acids. In one embodiment, one or both of X$_n$ or Z$_m$ consists of the sequence immediately flanking the LHAL (SEQ ID NO: 5) or GPIPIRRH (SEQ ID NO: 6) sequences in native human NESP55.

15. The invention also provides an isolated polypeptide comprising the amino acid sequence of SEQ ID NO:2, as well as isolated polypeptides comprising an amino acid sequence at least 90% identical to the amino acid sequence of SEQ ID NO: 2, or comprising an amino acid sequence at least 95% identical to the amino acid sequence of SEQ ID NO: 2, or comprising an amino acid sequence at least 98% identical to the amino acid sequence of SEQ ID NO: 2, or comprising an amino acid sequence at least 99.5% identical to the amino acid sequence of SEQ ID NO: 2. Isolated peptides consisting of the amino acid sequence LHAL (SEQ ID NO: 5) or the amino acid sequence GPIPIRRH (SEQ ID NO: 6) are also provided.

Another aspect of the invention pertains to isolated polynucleotides encoding or complementary to a polynucleotide encoding the polypeptides of the invention, e.g. encoding human NESP55 or encoding SEQ ID NO: 2. In a preferred embodiment, the isolated polynucleotide comprises the nucleotide of SEQ ID NO: 1. In another preferred embodiment, the polynucleotide is suitable for expressing the polypeptide of the invention in a host cell. The invention further provides vector constructs comprising the polynucleotides of the invention, and host cells transformed with the vector constructs of the invention. Still further, methods of making human NESP55 polypeptide, comprising culturing a host cell of the invention and isolating the human NESP55 polypeptide from the host cell, or culture medium, are also provided. Polypeptides obtainable by these methods are also encompassed by the invention.

Yet another aspect of the invention pertains to antibodies reactive towards the polypeptides of the invention. In one embodiment, the antibody is reactive towards the peptide sequence LHAL (SEQ ID NO: 5) and GAIPIPIRRH (SEQ ID NO: 6).

Pharmaceutical compositions, comprising an antibody of the invention, a NESP55 polypeptide of the invention or a NESP55 processed polypeptide of the invention, as well as a pharmaceutically acceptable carrier, are also provided. Methods of treating or preventing obesity in a patient, the method comprising administering to the patient an effective amount of an antibody of the invention, a NESP55 polypeptide of the invention, a NESP55 processed polypeptide of the invention or a pharmaceutical composition of the invention are also provided.

Another aspect of the invention pertains to a method of identifying a polypeptide (interacting polypeptide) that is capable of interacting with a human NESP55, or a processed polypeptide thereof. The method comprises the steps of (1) exposing the polypeptide to a test composition that may comprise an interacting polypeptide, (2) detecting an interaction between the polypeptide and an interacting polypeptide and optionally (3) identifying and/or isolating the interacting polypeptide. A substantially pure interacting polypeptide identified or identifiable by the method of the invention is also provided.

Another aspect of the invention pertains to a method of identifying a compound capable of disrupting or preventing the interaction between a human NESP55 polypeptide, or a processed polypeptide thereof or a GAIPIRRH (SEQ ID NO: 4)-containing polypeptide, and an interacting polypeptide. In the method, the human NESP55 polypeptide, or processed polypeptide thereof or the GAIPIRRH (SEQ ID NO: 4)-containing polypeptide, and the interacting polypeptide are exposed to the compound and the interaction between the human NESP55 polypeptide, or processed polypeptide thereof or the GAIPIRRH (SEQ ID NO: 4)-containing polypeptide, and the interacting polypeptide is measured in the presence and absence of the compound. Compounds identified by or identifiable by this method are also encompassed by the invention.

Still a further aspect of the invention pertains to a method of determining whether an individual is likely to become or remain obese or become more obese. The method comprises determining the level of NESP55 or a fragment derived or derivable from NESP55 or determining the level of a messenger RNA encoding NESP55, or the activity of NESP55 in a tissue sample, for example a body fluid, and determining that the level or activity differs from a level or activity found in an individual that is not obese and/or not expected to become obese. A kit of parts for determining whether an individual is likely to become or remain obese or become more obese the kit comprising means to determine the level of NESP55 or a fragment derived or derivable from NESP55 or means to determine the level of mRNA encoding NESP55 is also provided.

Another aspect of the invention pertains to a method of treating or preventing obesity in a patient, the method comprising administering to the patient an effective amount of an inhibitor of a polypeptide that is capable of cleaving NESP55. A compound capable of altering the expression of NESP55 is also encompassed by the invention, as well as a method of treating or preventing obesity in a patient, the method comprising administering to the patient an effective amount of a compound capable of altering the expression of NESP55.

Yet another aspect of the invention pertains to a method of identifying a compound capable of disrupting or preventing the interaction between the peptide LHAL (SEQ ID NO: 5) and human $5HT_{1B/1D}$ receptor wherein the LHAL(SEQ ID NO: 5)-containing polypeptide and/or the receptor are exposed to the compound and the interaction between the polypeptide and the receptor is measured in the presence and absence of the compound. A kit of parts comprising a LHAL (SEQ ID NO: 5)-containing peptide and human $5HT_{1B/1D}$ receptor is also provided. A compound identified by or identifiable by this method is also provided.

Another aspect of the invention pertains to a method of disrupting or preventing the interaction between the peptide LHAL (SEQ ID NO: 5) and human $5HT_{1B/1D}$ receptor. The method comprises exposing the human $5HT_{1B/1D}$ receptor to a compound identified by the above method or an antibody reactive against the peptide sequence LHAL (SEQ ID NO: 5). The invention also provides a method of treating or preventing obesity in a patient, the method comprising administering to the patient an effective amount of the compound identified by the above method or an antagonist of human $5HT_{1B/1D}$ receptor or an antibody reactive against the peptide sequence LHAL (SEQ ID NO: 5). The human $5HT_{1B/1D}$ receptor antagonist can be, for example, an anti-receptor antibody.

DETAILED DESCRIPTION OF THE INVENTION
I. POLYPEPTIDES

A first aspect of the invention provides a substantially pure polypeptide comprising the amino acid sequence

```
                                                    (SEQ ID NO: 2)
IRLEVPKRMDRRSRAQQWRRARHNYNDLCPPIGRRAATALLWLSCSIALL

RALATSNARAQQRAAAQQRRSFLNAHHRSGAQVFPESPESESDHEHEEAD

LELSLPECLEYEEEFDYETESETESEIESETDFETEPETAPTTEPETEPE

DDRGPVVPKHSTFGQSLTQRLHALKLRSPDASPSRAPPSTQEPQSPREGE

ELKPEDKDPRRDPEESKEPKEEKQRRRCKPKKPTRRDASPESPSKKGPIP

IRRH
``` or a variant, fragment, fusion or derivative thereof, or a fusion of a said variant or fragment or derivative, wherein the polypeptide variant has an amino acid sequence which has at least 90% identity with the amino acid sequence given above. Preferably, the polypeptide variant has an amino acid sequence which has at least 95%, more preferably at least 98%, and most preferably at least 99.5% identity with the amino acid sequence given above. The polypeptide whose amino acid sequence is shown above is considered to be human NESP55, although it may start at the Met residue at position 9 in the sequence. The said variant, fragment, fusion or derivative or a fusion of a said variant or fragment or derivative is not bovine NESP55 or mouse NESP55.

Standard IUPAC one and three letter codes are used for amino acid sequences used in the specification, and the amino acid sequences are listed N-terminal to C-terminal as is conventional.

Figure 1:
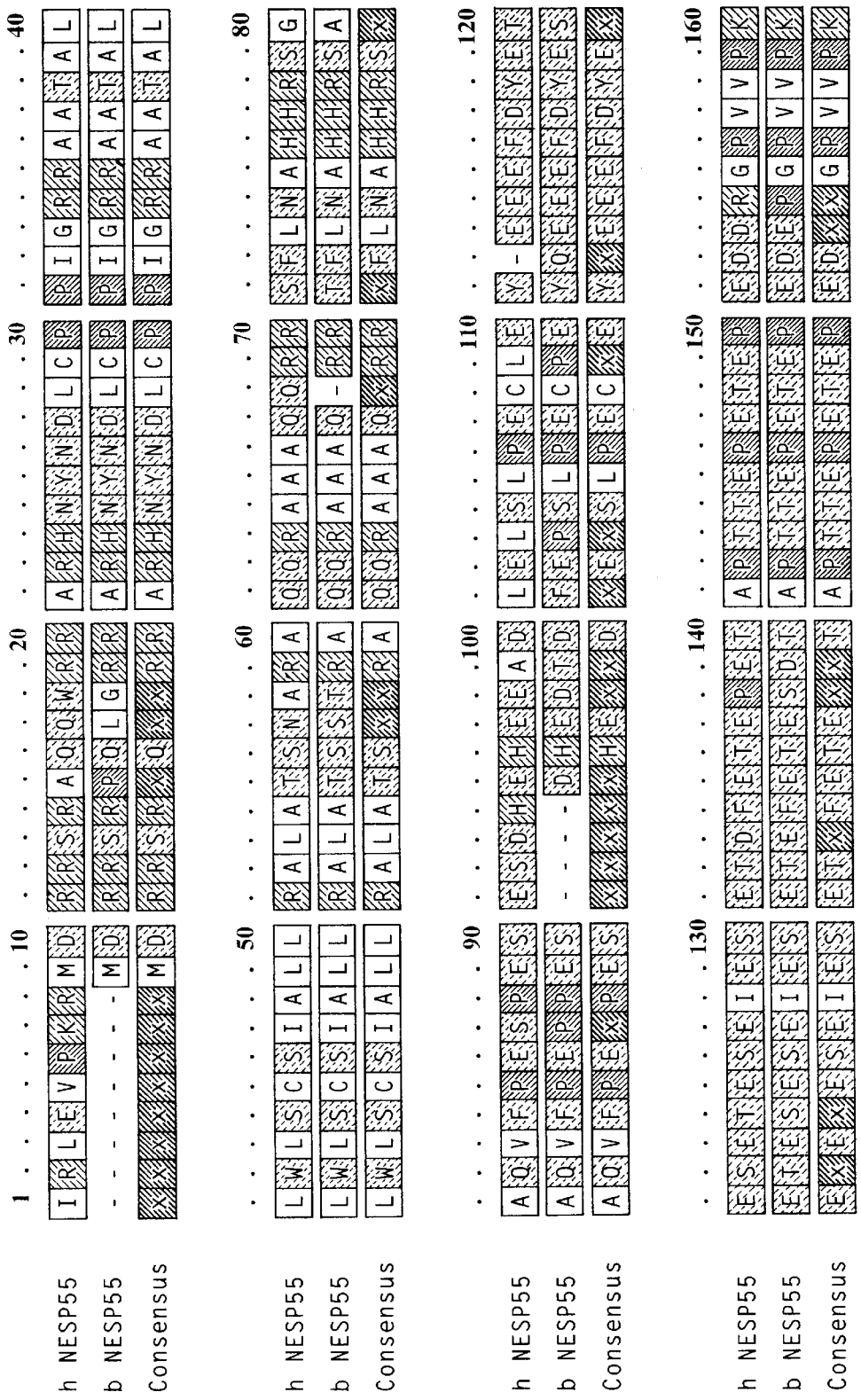
FIG. 1 (continued as FIG. 1a) is an alignment of the amino acid sequences of human NESP55 protein (SEQ ID NO: 2) and bovine NESP55 protein (SEQ ID NO: 15). The consensus sequence is also shown (SEQ ID NO: 16).
Figure 1A:
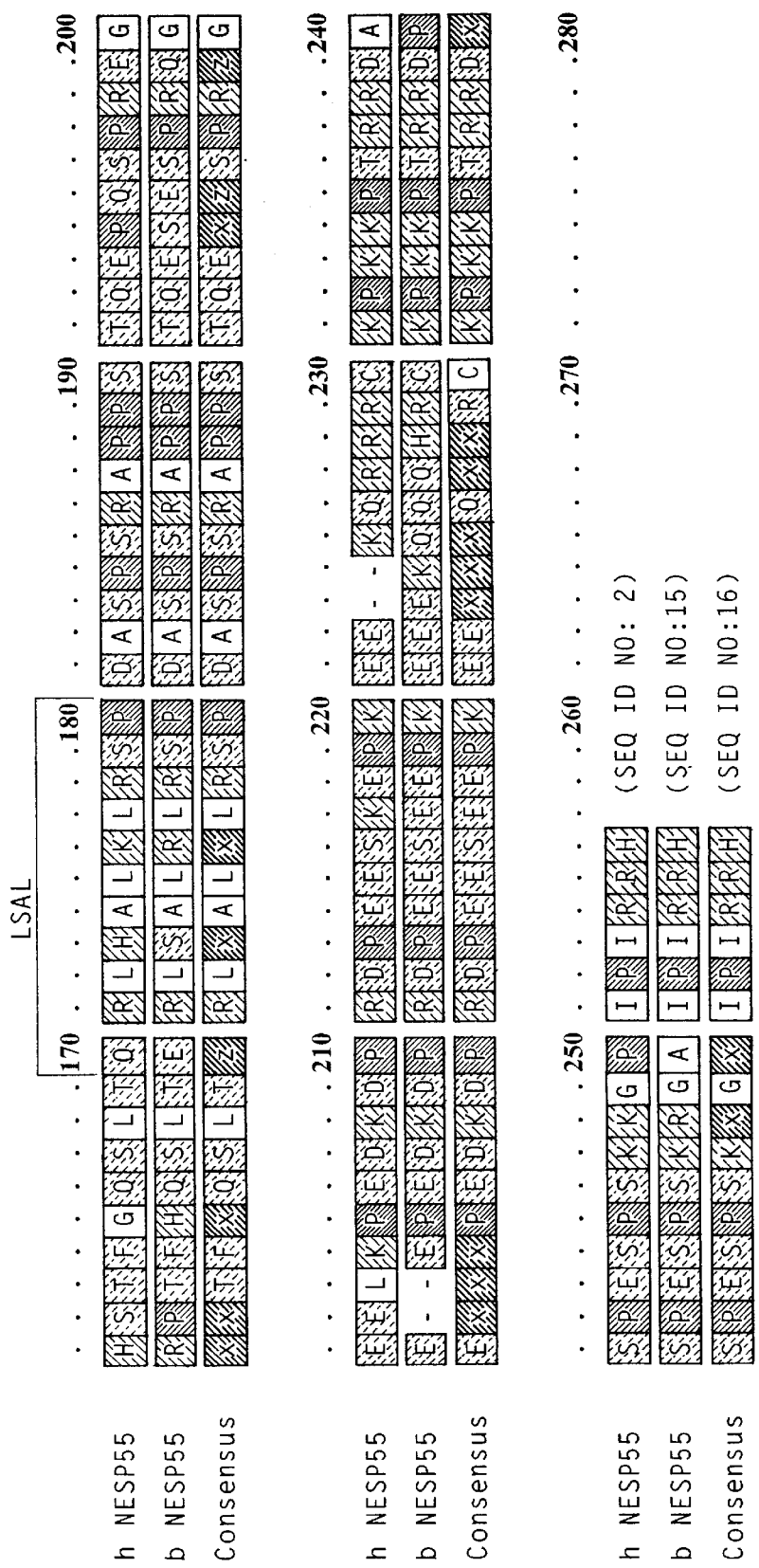

The amino acid sequence of human NESP55 is also shown in FIG. 1 (hNESP55) (SEQ ID NO: 2). The amino acid sequence of bovine NESP55 (Ischia et al (1997) (SEQ ID NO: 15) is also shown in FIG. 1 for comparison.

By "substantially pure" we mean that the said polypeptide is substantially free of other proteins. Thus, we include any composition that includes at least 30% of the protein content by weight as the said polypeptide, preferably at least 50%, more preferably at least 70%, still more preferably at least 90% and most preferably at least 95% of the protein content is the said polypeptide.

Thus, the invention also includes compositions comprising the said polypeptide and a contaminant wherein the contaminant comprises less than 70% of the composition by weight, preferably less than 50% of the composition, more preferably less than 30% of the composition, still more preferably less than 10% of the composition and most preferably less than 5% of the composition by weight.

The invention also pertains to "isolated" hNESPP55 polypeptides. An "isolated" or "purified" polypeptide or biologically active portion thereof is substantially free of cellular material or other contaminating proteins from the cell or tissue source from which the hNESP55 polypeptide is derived, or substantially free from chemical precursors or other chemicals when chemically synthesized. The language "substantially free of cellular material" includes preparations of hNESP55 polypeptide in which the polypeptide is separated from cellular components of the cells from which it is isolated or recombinantly produced. In one embodiment, the language "substantially free of cellular material" includes preparations of hNESP55 polypeptide having less than about 30% (by dry weight) of non-hNESP55 polypeptide (also referred to herein as a "contaminating protein"), more preferably less than about 20% of non-hNESP55 polypeptide, still more preferably less than about 10% of non-hNESP55 polypeptide, and most preferably less than about 5% non-hNESP55 polypeptide. When the hNESP55 polypeptide or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of hNESP55 polypeptide in which the polypeptide is separated from chemical precursors or other chemicals which are involved in the synthesis of the polypeptide. In one embodiment, the language "substantially free of chemical precursors or other chemicals" includes preparations of hNESP55 polypeptide having less than about 30% (by dry weight) of chemical precursors or non-hNESP55 polypeptide, more preferably less than about 20% chemical precursors or non-hNESP55 polypeptide, still more preferably less than about 10% chemical precursors or non-hNESP55 polypeptide, and most preferably less than about 5% chemical precursors or hNESP55 polypeptide.

The invention also includes the substantially pure said polypeptide when combined with other components ex vivo, said other components not being all of the components found in the cell in which said polypeptide is found. As is described below, the polypeptides of the invention can be produced using recombinant DNA technology.

Variants (whether naturally-occurring or otherwise) may be made using the methods of protein engineering and site-directed mutagenesis well known in the art using the recombinant polynucleotides described below.

By "fragment of said polypeptide" we include any fragment which retains biological activity or which is useful in some other way, for example, for use in raising antibodies or in a binding or other assay, or which fragment may have other functions as described in more detail below. Preferred fragments of human NESP55 are discussed further below.

By "fusion of said polypeptide" we include said polypeptide fused to any other polypeptide. For example, the said polypeptide may be fused to a polypeptide such as glutathione-S-transferase (GST) or protein A in order to facilitate purification of said polypeptide. Examples of such fusions are well known to those skilled in the art. Similarly, the said polypeptide may be fused to an oligo-histidine tag such as His6 or to an epitope recognised by an antibody such as the well known Myc tag epitope. Fusions to any variant, fragment or derivative of said polypeptide are also included in the scope of the invention. It will be appreciated that fusions which retain desirable properties, such as binding properties, an ability to be cleaved by suitable proteases, and other biological functions, of hNESP55 are particularly preferred. It is also particularly preferred if the fusions are one which are suitable for use in the screening assays described later. It will be appreciated that before the present invention, the requirement for relatively large amounts of hNESP55 or variants or fusions or derivatives thereof had not been appreciated in the art since the involvement of NESP55 in obesity was not known. In particular it was not appreciated that hNESP55 and variants and fusions thereof would be useful in screening methods for drugs and drug-like compounds.

By "variants" of the polypeptide we include insertions, deletions and substitutions, either conservative or non-conservative. In particular we include variants of the polypeptide where such changes do not substantially alter the activity of the said polypeptide. Variants of human NESP55 do not include polypeptides which have the amino acid sequence of bovine or mouse NESP55.

It will be appreciated that a variant that comprises substantially all of the sequence shown above (ie substantially full-length human NESP55) may be particularly useful. By "substantially all" is meant at least 80%, preferably 90%, still more preferably 95%, 98% or 100% (ie all) of the said sequence. By "substantially full-length" is meant comprising at least 80%, preferably 90%, still more preferably 95%, 98% or 100% (ie all) of the sequence of the full length polypeptide.

By "conservative substitutions" is intended combinations such as Gly, Ala; Val, Ile, Leu; Asp, Glu; Asn, Gln; Ser, Thr; Lys, Arg; and Phe, Tyr.

It is particularly preferred if the polypeptide variant has an amino acid sequence which has at least 90% identity with the amino acid sequence given above, more preferably at least 92%, still more preferably at least 95%, yet more preferably at least 96%, and most preferably at least 98% or 99% identity with the amino acid sequence given above.

The percent sequence identity between two polypeptides may be determined using suitable computer programs, for example the GAP program of the University of Wisconsin Genetic Computing Group and it will be appreciated that percent identity is calculated in relation to polypeptides whose sequences have been aligned optimally.

The alignment may alternatively be carried out using the Clustal W program (Thompson, J. D., Higgins, D. G. and Gibson, T. J. (1994), Clustal-W—improving the sensitivity of progressive multiple sequence alignment through sequence weighting, position specific gap penalties and weight matrix choice. *Nuc. Acid Res.* 22, 4673–4680).

The parameters used may be as follows:

Fast pairwise alignment parameters: K-tuple(word) size; 1, window size; 5, gap penalty; 3, number of top diagonals; 5. Scoring method: x percent.

Multiple alignment parameters: gap open penalty; 10, gap extension penalty; 0.05.

Scoring matrix: BLOSUM.

A particular embodiment of the invention provides a substantially pure human NESP55 polypeptide which consists of the amino acid sequence

```
                                              (SEQ ID NO: 2)
IRLEVPKRMDRRSRAQQWRRARHNYNDLCPPIGRRAATALLWLSCSIALL

RALATSNARAQQRAAAQQRRSFLNAHHRSGAQVFPESPESESDHEHEEAD

LELSLPECLEYEEEFDYETESETESEIESETDFETEPETAPTTEPETEPE

DDRGPVVPKHSTFGQSLTQRLHALKLRSPDASPSRAPPSTQEPQSPREGE

ELKPEDKDPRRDPEESKEPKEEKQRRRCKPKKPTRRDASPESPSKKGPIP

IRRH
``` or naturally occurring allelic variants thereof.

It is particularly preferred, although not essential, that the variant or fragment or derivative or fusion of the said polypeptide, or the fusion of the variant or fragment or derivative comprises the amino acid sequence LHAL (SEQ ID NO: 5) and/or the amino acid sequence GPIPIRRH (SEQ ID NO: 6). It is more preferred that the variant or fragment or derivative or fusion of the said polypeptide, or the fusion of the variant or fragment or derivative has at least one sequence of two or more consecutive basic amino acid residues at a position equivalent to two or more consecutive basic amino acid residues present in the amino acid sequence of full length human NESP55. Such two or more consecutive basic amino acid residues are present at positions 11–12, 19–20, 34–35, 69–70, 225–227, 231–232, 235–236, 245–246 and 252–253 of full length human NESP55 as shown in FIG. 1 and in SEQ ID NO: 2.

By "residue equivalent to" a particular residue, for example the residue Lys245 of full-length human NESP55, is included the meaning that the amino acid residue occupies a position in the native two or three dimensional structure of a polypeptide corresponding to the position occupied by the said particular residue, for example Lys245, in the native two or three dimensional structure of full-length human NESP55.

The residue equivalent to a particular residue, for example Lys245 of full-length human NESP55, may be identified by alignment of the sequence of the polypeptide with that of full-length human NESP55 in such a way as to maximise the match between the sequences. The alignment may be carried out by visual inspection and/or by the use of suitable computer programs, for example the GAP program of the University of Wisconsin Genetic Computing Group, which will also allow the percent identity of the polypeptides to be calculated, or using the Align program (Pearson (1994) in: Methods in Molecular Biology, Computer Analysis of Sequence Data, Part II (Griffin, A M and Griffin, H G eds) pp 365–389, Humana Press, Clifton). Thus, residues identified in this manner are also "equivalent residues".

It will be appreciated that in the case of truncated forms of human NESP55 or in forms where simple replacements of amino acids have occurred it is facile to identify the "equivalent residue".

A further aspect of the invention provides a polypeptide (which, for convenience, we generally term "processed polypeptide") derivable from the polypeptide of the invention (human NESP55) wherein the said processed polypeptide is derivable, or predicted from the amino acid sequence of human NESP55 to be derivable, by endoproteolytic cleavage of the said polypeptide of the invention. The said endoproteolytic cleavage or cleavages may be a cleavage or cleavages that may be performed by a trypsin-like or subtilisin-like endoprotease. Thus, (1) the N-terminal amino acid of the processed polypeptide may be immediately preceded (in the sequence of human NESP55) by a cleavage site for a trypsin-like or subtilisin-like endoprotease, for example a prohormone convertase or endoprotease and/or (2) the C-terminus of the processed polypeptide may immediately precede (in the sequence of human NESP55) a cleavage site for a trypsin-like or subtilisin-like endoprotease, for example a prohormone convertase or endoprotease.

Examples of trypsin-like or subtilisin-like endoproteases include the prohormone convertases PC1, PC2 and furin (see, for example Christie et al (1991) Identification of kex2-related proteases in chromaffin granules by partial amino acid sequence analysis. *J Biol Chem* 266, 15679–15683; Egger et al (1993). Different degrees of processing of secretogranin II in large dense core vesicles of bovine adrenal medulla and symathetic axons correlate with their content of soluble PC1 and PC2. *Neurosci Lett* 159, 199–201; Kirchmair et al (1992) Differential subcellular distribution of PC1, PC2 and furin in bovine adrenal medulla and secretion of PC1 and PC2 from this tissue. *Neurosci Lett* 143, 143–154; references in Lovisetti-Scamihorn et al (1999) *Brain Res* 829, 99–106; references in Lovisetti-Scamihorn et al (1999) *Reg Peptides* 79, 63–67). Furin (also known as PACE; paired basic amino acid cleaving enzyme; Wise et al (1990) PNAS 87, 9378–9382 and Fuller et al (1989) *Science* 246, 482–486) is related to Kex2, a subtilisin-like protease from yeast that cleaves prepro-killer toxin and prepro-α-factor at the paired amino acid sequence Lys-Arg and Arg-Arg. Trypsin-like endoproteases may cleave after a single basic amino acid.

The N-terminal amino acid residue of the said processed polypeptide may be immediately preceded in the amino acid sequence of human NESP55 by two consecutive basic amino acid residues (ie a pair of basic amino acids) or by a basic amino acid residue. Basic amino acids include lysine, arginine and histidine. It is preferred that a said basic amino acid residue is not a histidine residue. Similarly, the C-terminus of the said processed polypeptide may be immediately preceded by two consecutive basic amino acid residues or by a basic amino acid residue.

Polypeptides which are considered to be examples of said processed polypeptides include a polypeptide consisting of the amino acid sequence LHAL (SEQ ID NO: 5) and a polypeptide consisting of the amino acid sequence GPIPIRRH (SEQ ID NO: 6).

A further preferred processed polypeptide may have the N-terminal sequence SFLN (SEQ ID NO: 7), corresponding to amino acids 71 to 74 of the amino acid sequence of human NESP55, as shown in FIG. 1 and in SEQ ID NO: 2. The said polypeptide may not comprise the amino acid sequence, for example the C-terminal amino acid sequence GPIPIRRH (SEQ ID NO: 6). The polypeptide may have the C-terminal sequence PSKK (SEQ ID NO: 8), corresponding to amino acids 243 to 246 of the amino acid sequence of human NESP55, as shown in FIG. 1 and SEQ ID NO: 2.

A further preferred processed polypeptide may have the C-terminal sequence PSKK (SEQ ID NO: 8), corresponding to amino acids 243 to 246 of the amino acid sequence of human NESP55, as shown in FIG. 1 and SEQ ID NO: 2. The polypeptide may have the N-terminal sequence of human NESP55. This may be the N-terminal sequence of human NESP55 as translated from the most 5N in frame methionine codon (ie MDRR; SEQ ID NO: 9) or the N-terminal sequence of human NESP55 following removal of the signal sequence (ie ATAL; SEQ ID NO: 10), which consist of the first 36 amino acids of the sequence of human NESP55 shown in FIG. 1 or in SEQ ID NO: 2.

A said processed polypeptide, for example GPIPIRRH (SEQ ID NO: 6), may be useful, for example as a neuropeptide or as a ligand for a neuropeptide receptor or as a means for identifying a neuropeptide receptor. A further said processed polypeptide LHAL (SEQ ID NO: 5) may be useful, for example as a 5-HT$_{1B}$ receptor antagonist or for identifying a 5-HT$_{1B}$ receptor antagonist or agonist. A said processed polypeptide or human NESP55 may be useful in medicine, for example in the treatment or prophylaxis of obesity, or in the identification or preparation of a compound that may be useful in medicine, for example in the treatment or prophylaxis of obesity. These aspects of the invention are discussed more fully below.

It will be appreciated that although the processed polypeptides may be derived from human NESP55 by proteolytic processing as described above, it will generally be more convenient to derive the desired sequence intellectually and/or empirically from the human NESP55 amino acid sequence, and to then synthesise the peptide.

Peptides may be synthesised by the Fmoc-polyamide mode of solid-phase peptide synthesis as disclosed by Lu et al (1981) J Org. Chem. 46, 3433 and references therein. Temporary N-amino group protection is afforded by the 9-fluorenylmethyloxycarbonyl (Fmoc) group. Repetitive cleavage of this highly base-labile protecting group is effected using 20% piperidine in N,N-dimethylformamide. Side-chain functionalities may be protected as their butyl ethers (in the case of serine threonine and tyrosine), butyl esters (in the case of glutamic acid and aspartic acid), butyloxycarbonyl derivative (in the case of lysine and histidine), trityl derivative (in the case of cysteine) and 4-methoxy-2,3,6-trimethylbenzenesulphonyl derivative (in the case of arginine). Where glutamine or asparagine are C-terminal residues, use is made of the 4,4'-dimethoxybenzhydryl group for protection of the side chain amido functionalities. The solid-phase support is based on a polydimethyl-acrylamide polymer constituted from the three monomers dimethylacrylamide (backbone-monomer), bisacryloylethylene diamine (cross linker) and acryloylsarcosine methyl ester (functionalising agent). The peptide-to-resin cleavable linked agent used is the acid-labile 4-hydroxymethyl-phenoxyacetic acid derivative. All amino acid derivatives are added as their preformed symmetrical anhydride derivatives with the exception of asparagine and glutamine, which are added using a reversed N,N-dicyclohexyl-carbodiimide/1-hydroxybenzotriazole mediated coupling procedure. All coupling and deprotection reactions are monitored using ninhydrin, trinitrobenzene sulphonic acid or isotin test procedures. Upon completion of synthesis, peptides are cleaved from the resin support with concomitant removal of side-chain protecting groups by treatment with 95% trifluoroacetic acid containing a 50% scavenger mix. Scavengers commonly used are ethanedithiol, phenol, anisole and water, the exact choice depending on the constituent amino acids of the peptide being synthesised. Trifluoroacetic acid is removed by evaporation in vacuo, with subsequent trituration with diethyl ether affording the crude peptide. Any scavengers present are removed by a simple extraction procedure which on lyophilisation of the aqueous phase affords the crude peptide free of scavengers. Reagents for peptide synthesis are generally available from Calbiochem-Novabiochem (UK) Ltd, Nottingham NG7 2QJ, UK. Purification may be effected by any one, or a combination of, techniques such as size exclusion chromatography, ion-exchange chromatography and (principally) reverse-phase high performance liquid chromatography. Analysis of peptides may be carried out using thin layer chromatography, reverse-phase high performance liquid chromatography, amino-acid analysis after acid hydrolysis and by fast atom bombardment (FAB) mass spectrometric analysis.

It will be appreciated that the processed peptides of the invention may be comprised within a further sequence such that the flanking sequences may or may not be the flanking sequences in human NESP55. For example, a further aspect of the invention provides a polypeptide containing the sequence LHAL (SEQ ID NO: 5) whether or not the flanking sequences are those flanking LHAL (SEQ ID NO: 5) in native human NESP55. A still further aspect of the invention provides a polypeptide containing the sequence GPIPIRRH (SEQ ID NO: 6) whether or not the flanking sequences are those flanking GPIPIRRH (SEQ ID NO: 6) in native human NESP55.

The polypeptides of these aspects of the invention typically consist of the amino acid sequence X$_n$LHALZ$_m$ (SEQ ID NO: 11), or X$_n$GPIPIRRHZ$_m$ (SEQ ID NO: 12) wherein X$_n$ represents the amino acid sequence of the consecutive n amino acids immediately N terminal to the amino acid sequence LHAL (SEQ ID NO: 5) or GPIPIRRH (SEQ ID NO: 6) and wherein Z$_m$ represents the amino acid sequence of the consecutive m amino acids immediately C terminal to the amino acid sequence LHAL (SEQ ID NO: 5) or GPIPIRRH (SEQ ID NO: 6), wherein n and m may independently be any number between 0 and 1, 5, 10, 15, 20, 25 and 30 amino acids, preferably between 0 and 20, still more preferably between 0 and 10 amino acids. It is preferred that the amino acid sequences X$_n$ and Z$_m$ are those found immediately N and C terminal, respectively, to the amino acid sequence LHAL (SEQ ID NO: 5) or GPIPIRRH (SEQ ID NO: 6) in native human NESP55. It is preferred that the amino acids are L-amino acids, in particular it is preferred that the LHAL (SEQ ID NO: 5) or GPIPIRRH (SEQ ID NO: 6) motifs consist of L-amino acid residues. It is preferred that the amino acid residues immediately flanking (such as those within 10 to 20 residues) of the motif are L-amino acids residues, but that they may be D-amino acid residues. It will be appreciated that similar peptides are included in the invention in which the core motif (such as LHAL {SEQ ID NO: 5} and GPIPIRRH {SEQ ID NO: 5}, as described above), is another peptide which is derivable by processing of human NESP55 as described above.

A further aspect of the invention provides a recombinant polynucleotide encoding a polypeptide as defined in the first aspect of the invention or encoding a variant or fragment (which term it will be appreciated includes a processed polypeptide as defined above, as well as the polypeptides described above which have a processed polypeptide as the core motif and flanking regions as described above) or derivative or fusion of said polypeptide or a fusion of a said variant or fragment or derivative. Preferences and exclusions for the said polynucleotide variant are preferences for, and exclusions of, polynucleotides which encode the same polypeptides as in the first aspect of the invention, except that the following Expressed Sequence Tag (EST) is also excluded: IMAGE clone 746837.

II. Polynucleotides

A further aspect of the invention provides a recombinant polynucleotide suitable for expressing a polypeptide as defined in the first aspect of the invention or suitable for expressing a variant or fragment or derivative of fusion of said polypeptide or a fusion of a said variant or fragment or derivative. Preferences and exclusions for the said polynucleotide variant are preference for, and exclusions of, polynucleotides which encode the same polypeptides as in the first aspect of the invention and in relation to the processed polypeptides of the invention.

By "suitable for expressing" is meant that the polynucleotide is a polynucleotide that may be translated to form the polypeptide, for example RNA, or that the polynucleotide (which is preferably DNA) encoding the polypeptide of the invention is inserted into an expression vector, such as a plasmid, in proper orientation and correct reading frame for expression. The polynucleotide may be linked to the appropriate transcriptional and translational regulatory control nucleotide sequences recognised by any desired host; such controls may be incorporated in the expression vector.

It is not considered that the EST listed above (ie IMAGE clone 746837) is a polynucleotide as defined above; however, for the avoidance of doubt, the EST excluded above is further excluded from this aspect of the invention.

The invention also pertains to "isolated" hNESP55 nucleic acid molecules. The term "isolated nucleic acid molecule" includes nucleic acid molecules which are separated from other nucleic acid molecules which are present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated NESP55 nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

A further aspect of the invention is a replicable vector suitable for expressing a polypeptide as defined in the first aspect of the invention or suitable for expressing a variant or fragment or derivative of fusion of said polypeptide or a fusion of a said variant or fragment or derivative. Preferences and exclusions for the said polynucleotide variant are preferences for, and exclusions of, polynucleotides which encode the same polypeptides as in the first aspect of the invention. For example, the replicable vector may be suitable for expressing a fusion of the polypeptide as defined in the first aspect of the invention, in particular a GST fusion.

A further aspect of the invention is a polynucleotide encoding a fusion of the polypeptide as defined in the first aspect of the invention, or a fusion of a variant or fragment or derivative, in particular a GST fusion. A still further aspect is a vector suitable for replication in a eukaryotic, preferably mammalian, cell, comprising a polynucleotide encoding the polypeptide, or a variant or fragment or derivative or a fusion of the polypeptide, as defined in the first aspect of the invention, or a fusion of a variant or fragment or derivative, in particular a GST fusion. The following ESTs clones may be vectors which may be suitable for replication in a mammalian/eukaryotic cell and are excluded from this aspect of the invention: AA389168; AA678670. It is not considered that any other of the ESTs excluded from other aspects of the invention are vectors as defined above; however, it will be appreciated that any other of the ESTs clones that may be such a vector are also excluded.

Characteristics of vectors suitable for replication in mammalian/eukaryotic cells are well known to those skilled in the art. It will be appreciated that a vector may be suitable for replication in both prokaryotic and eukaryotic cells.

In one preferred embodiment the polynucleotide comprises the nucleotide sequence:

```
GAATTCGGCTCGAGGTGCCTAAGAGGATGGATCGGAGGTCCCGGGCTCAGCAGTGGCGCC

GAGCTCGCCATAATTACAACGACCTGTGCCCGCCCATAGGCCGCCGGGCAGCCACCGCGC

TCCTCTGGCTCTCCTGCTCCATCGCGCTCCTCCGCGCCCTTGCCACCTCCAACGCCCGTG

CCCAGCAGCGCGCGGCTGCCCAACAGCGCCGGAGCTTCCTTAACGCCCACCACCGCTCCG

GCGCCCAGGTATTCCCTGAGTCCCCCGAATCGGAATCTGACCACGAGCACGAGGAGGCAG

ACCTTGAGCTGTCCCTCCCCGAGTGCCTAGAGTACGAGGAAGAGTTCGACTACGAGACCG

AGAGCGAGACCGAGTCCGAAATCGAGTCCGAGACCGACTTCGAGACCGAGCCTGAGACCG

CCCCCACCACTGAGCCCGAGACCGAGCCTGAAGACGATCGCGGCCCGGTGGTGCCCAAGC

ACTCCACCTTCGGCCAGTCCCTCACCCAGCGTCTGCACGCTCTCAAGTTGCGAAGCCCCG

ACGCCTCCCCAAGTCGCGCGCCGCCCAGCACTCAGGAGCCCCAGAGCCCCAGGGAAGGGG
```

-continued

```
AGGAGCTCAAGCCCGAGGACAAAGATCCAAGGGACCCCGAAGAGTCGAAGGAGCCCAAGG

AGGAGAAGCAGCGGCGTCGCTGCAAGCCAAAGAAGCCCACCCGCCGTGACGCGTCCCCGG

AGTCCCCTTCCAAAAAGGGACCCATCCCCATCCGGCGTCACTAATGGAGGACGCCGTCCA

GATTCTCCTTGTTTTCATGGATTCAGGTGCTGGAGAATCTGGTAAAAGCACCATTGTGAA

GCAGATGAGGATCCTGCATGTTAATGGGTTTAATGGAGAGGGCGGCGAAGAGGACCCGCA

GGCTGCAAGGAGCAACAGCGATGGTGAGAAGGCAACCAAAGTGCAGGACATCAAAAACAA

CCTGAAAGAGGCGATTGAAACCATTGTGGCCGCCATGAGCAACCTGGTGCCCCCCGTGGA

GCTGGCCAACCCCGAGAACCAGTTCAGAGTGGACTACATTCTGAGTGTGATGAACGTGCC

TGACTTTGACTTCCCTCCCGAATTCTATGAGCATGCCAAGGCTCTGTGGGAGGATGAAGG

AGTGCGTGCCTGCTACGAACGCTCCAACGAGTACCAGCTGATTGACTGTGCCCAGTACTT

CCTGGACAAGATCGACGTGATCAAGCAGGCTGACTATGTGCCGAGCGATCAGGACCTGCT

TCGCTGCCGTGTCCTGACTTCTGGAATCTTTGAGACCAAGTTCCAGGTGGACAAAGTCAA

CTTCCACATGTTTGACGTGGGTGGCCAGCGCGATGAACGCCGCAAGTGGATCCAGTGCTT

CAACGATGTGACTGCCATCATCTTCGTGGTGGCCAGCAGCAGCTACAACATGGTCATCCG

GGAGGACAACCAGACCAACCGCCTGCAGGAGGCTCTGAACCTCTTCAAGAGCATCTGGAA

CAACAGATGGCTGCGCACCATCTCTGTGATCCTGTTCCTCAACAAGCAAGATCTGCTCGC

TGAGAAAGTCCTTGCTGGGAAATCGAAGATTGAGGACTACTTTCCAGAATTTGCTCGCTA

CACTACTCCTGAGGATGCTACTCCCGAGCCCGGAGAGGACCCACGCGTGACCCGGGCCAA

GTACTTCATTCGAGATGAGTTTCTGAGGATCAGCACTGCCAGTGGAGATGGGCGTCACTA

CTGCTACCCTCATTTCACCTGCGCTGTGGACACTGAGAACATCCGCCGTGTGTTCAACGA

CTGCCGTGACATCATTCAGCGCATGCACCTTCGTCAGTACGAGCTGCTCTAAGAAGGGAA

CCCCCAAATTTAATTAAAGCCTTAAGCACAATTAATTAAAAGTGAAACGTAATTGTACAA

GCAGTTAATCACCCACCATAGGGCATGATTAACAAAGCAACCTTTCCCTTCCCCCGAGTG

ATTTTGCGAAACCCCCTTTTCCCTTCAGCTTGCTTAGATGTTCCAAATTTAGAAAGCTTA

AGGCGGCCTACAGAAAAAGGAAAAAAGGCCACAAAAGTTCCCTCTCACTTTCAGTAAAAA

TAAATAAAACAGCAGCAGCAAACAAATAAAATGAAATAAAAGAAACAAATGAAATAAATA

TTGTGTTGTGCAGCATTAAAAAAAATCAAAATAAAAATTAAATGTGAGCAAAAAAAAAAA

AAAAAGGGCGGCCGC
```

(SEQ ID NO: 1)
or a variant, fragment, fusion or derivative thereof.

It will be appreciated that an expressed sequence tag (EST) clone is not a recombinant polynucleotide as defined above as it lacks sequences necessary for the translation and therefore expression of the expressed sequence tag. EST sequences may be cloned in the vector Uni-ZAP XR, pT7T3D-Pac, pBluescript SK-, Lafmid BA or pCMV-SPORT2 vector.

A polynucleotide comprising a fragment of the recombinant polynucleotide encoding a polypeptide of the invention or a variant, fragment, fusion or derivative may also be useful. Preferably, the polynucleotide comprises a fragment which is at least 10 nucleotides in length, more preferably at least 14 nucleotides in length and still more preferably at least 18 nucleotides in length. Such polynucleotides are useful as PCR primers. A polynucleotide complementary to the polynucleotide (or a fragment thereof) encoding a polypeptide of the invention or a variant, fragment, fusion or derivative may also be useful. Such complementary polynucleotides are well known to those skilled in the art as antisense polynucleotides.

The polynucleotide or recombinant polynucleotide of the invention may be DNA or RNA, preferably DNA. The polynucleotide may or may not contain introns in the coding sequence; preferably the polynucleotide is a cDNA.

A "variation" of the polynucleotide includes one which is (i) usable to produce a protein or a fragment thereof which is in turn usable, for example a processed polypeptide as described above, or to prepare antibodies which specifically bind to the protein encoded by the said polynucleotide or (ii) an antisense sequence corresponding to the gene or to a variation of type (i) as just defined. For example, different codons can be substituted which code for the same amino acid(s) as the original codons. Alternatively, the substitute codons may code for a different amino acid that will not affect the activity or immunogenicity of the protein or which may improve or otherwise modulate its activity or immunogenicity. For example, site-directed mutagenesis or other techniques can be employed to create single or multiple mutations, such as replacements, insertions, deletions, and transpositions, as described in Botstein and Shortle, "Strategies and Applications of In Vitro Mutagenesis" *Science*, 229: 193–210 (1985), which is incorporated herein by reference. Since such modified polynucleotides can be obtained by the application of known techniques to the teachings contained herein, such modified polynucleotides are within the scope of the claimed invention.

Moreover, it will be recognised by those skilled in the art that the polynucleotide sequence (or fragments thereof) encoding a polypeptide of the invention can be used to obtain other polynucleotide sequences that hybridise with it under conditions of high stringency. Such polynucleotides includes any genomic DNA. Accordingly, the polynucleotide of the invention includes polynucleotide that shows at least 80%, preferably 85%, and more preferably at least 90% and most preferably at least 95% homology with the polynucleotide identified in the method of the invention, provided that such homologous polynucleotide encodes a polypeptide which is usable in at least some of the methods described below or is otherwise useful. It will be appreciated that a polynucleotide encoding bovine NESP55 or mouse NESP55 is not a polynucleotide of the invention.

Percent homology can be determined by, for example, the GAP program of the University of Wisconsin Genetic Computer Group.

DNA-DNA, DNA-RNA and RNA-RNA hybridisation may be performed in aqueous solution containing between 0.1×SSC and 6×SSC and at temperatures of between 55° C. and 70° C. It is well known in the art that the higher the temperature or the lower the SSC concentration the more stringent the hybridisation conditions. By "high stringency" we mean 2×SSC and 65° C. 1×SSC is 0.15M NaCl/0.015M sodium citrate. Polynucleotides which hybridise at high stringency are included within the scope of the claimed invention.

"Variations" of the polynucleotide also include polynucleotide in which relatively short stretches (for example 20 to 50 nucleotides) have a high degree of homology (at least 80% and preferably at least 90 or 95%) with equivalent stretches of the polynucleotide of the invention even though the overall homology between the two polynucleotides may be much less. This is because important active or binding sites may be shared even when the general architecture of the protein is different.

A variety of methods have been developed to operably link polynucleotides, especially DNA, to vectors for example via complementary cohesive termini. Suitable methods are described in Sambrook et al(1989) Molecular Cloning, A Laboratory Manual, Cold Spring Harbor Laboratory, Cold Spring Harbor, N.Y.

A desirable way to modify the DNA encoding a polypeptide of the invention is to use the polymerase chain reaction as disclosed by Saiki et al (1988) *Science* 239, 487–491. This method may be used for introducing the DNA into a suitable vector, for example by engineering in suitable restriction sites, or it may be used to modify the DNA in other useful ways as is known in the art.

In this method the DNA to be enzymatically amplified is flanked by two specific primers which themselves become incorporated into the amplified DNA. The said specific primers may contain restriction endonuclease recognition sites which can be used for cloning into expression vectors using methods known in the art.

The DNA (or in the case of retroviral vectors, RNA) is then expressed in a suitable host to produce a polypeptide comprising the compound of the invention. Thus, the DNA encoding the polypeptide constituting the compound of the invention may be used in accordance with known techniques, appropriately modified in view of the teachings contained herein, to construct an expression vector, which is then used to transform an appropriate host cell for the expression and production of the polypeptide of the invention. Such techniques include those disclosed in U.S. Pat. No. 4,440,859 issued Apr. 3, 1984 to Rutter et al, U.S. Pat. No. 4,530,901 issued Jul. 23, 1985 to Weissman, U.S. Pat. No. 4,582,800 issued Apr. 15, 1986 to Crowl, U.S. Pat. No. 4,677,063 issued Jun. 30, 1987 to Mark et al, U.S. Pat. No. 4,678,751 issued Jul. 7, 1987 to Goeddel, U.S. Pat. No. 4,704,362 issued Nov. 3, 1987 to Itakura et al, U.S. Pat. No. 4,710,463 issued Dec. 1, 1987 to Murray, U.S. Pat. No. 4,757,006 issued Jul. 12, 1988 to Toole, Jr. et al, U.S. Pat. No. 4,766,075 issued Aug. 23, 1988 to Goeddel et al and U.S. Pat. No. 4,810,648 issued Mar. 7, 1989 to Stalker, all of which are incorporated herein by reference.

The DNA (or in the case of retroviral vectors, RNA) encoding the polypeptide constituting the compound of the invention may be joined to a wide variety of other DNA sequences for introduction into an appropriate host. The companion DNA will depend upon the nature of the host, the manner of the introduction of the DNA into the host, and whether episomal maintenance or integration is desired.

Generally, the DNA is inserted into an expression vector, such as a plasmid, in proper orientation and correct reading frame for expression. If necessary, the DNA may be linked to the appropriate transcriptional and translational regulatory control nucleotide sequences recognised by the desired host, although such controls are generally available in the expression vector. The vector is then introduced into the host through standard techniques. Generally, not all of the hosts will be transformed by the vector. Therefore, it will be necessary to select for transformed host cells. One selection technique involves incorporating into the expression vector a DNA sequence, with any necessary control elements, that codes for a selectable trait in the transformed cell, such as antibiotic resistance. Alternatively, the gene for such selectable trait can be on another vector, which is used to co-transform the desired host cell.

Host cells that have been transformed by the recombinant DNA of the invention are then cultured for a sufficient time and under appropriate conditions known to those skilled in the art in view of the teachings disclosed herein to permit the expression of the polypeptide, which can then be recovered.

Many expression systems are known, including bacteria (for example *E. coli* and *Bacillus subtilis*), yeasts (for example *Saccharomyces cerevisiae*), filamentous fungi (for example Aspergillus), plant cells, animal cells and insect cells.

The vectors include a prokaryotic replicon, such as the ColE1 ori, for propagation in a prokaryote, even if the vector is to be used for expression in other, non-prokaryotic, cell types. The vectors can also include an appropriate promoter such as a prokaryotic promoter capable of directing the expression (transcription and translation) of the genes in a bacterial host cell, such as *E. coli*, transformed therewith.

A promoter is an expression control element formed by a DNA sequence that permits binding of RNA polymerase and transcription to occur. Promoter sequences compatible with exemplary bacterial hosts are typically provided in plasmid vectors containing convenient restriction sites for insertion of a DNA segment of the present invention.

Typical prokaryotic vector plasmids are pUC18, pUC19, pBR322 and pBR329 available from Biorad Laboratories, (Richmond, Calif., USA) and pTrc99A and pKK223-3 available from Pharmacia, Piscataway, N.J., USA.

A typical mammalian cell vector plasmid is pSVL available from Pharmacia, Piscataway, N.J., USA. This vector uses the SV40 late promoter to drive expression of cloned genes, the highest level of expression being found in T antigen-producing cells, such as COS-1 cells.

An example of an inducible mammalian expression vector is pMSG, also available from Pharmacia. This vector uses the glucocorticoid-inducible promoter of the mouse mammary tumour virus long terminal repeat to drive expression of the cloned gene.

Useful yeast plasmid vectors are pRS403–406 and pRS413–416 and are generally available from Stratagene Cloning Systems, La Jolla, Calif. 92037, USA. Plasmids pRS403, pRS404, pRS405 and pRS406 are Yeast Integrating plasmids (YIps) and incorporate the yeast selectable markers HIS3, TRP1, LEU2 and URA3. Plasmids pRS413–416 are Yeast Centromere plasmids (YCps).

The present invention also relates to a host cell transformed with a polynucleotide vector construct of the present invention. The host cell can be either prokaryotic or eukaryotic. Bacterial cells are preferred prokaryotic host cells and typically are a strain of *E. coli* such as, for example, the *E. coli* strains DH5 available from Bethesda Research Laboratories Inc., Bethesda, Md., USA, and RR1 available from the American Type Culture Collection (ATCC) of Rockville, Md., USA (No ATCC 31343). Preferred eukaryotic host cells include yeast, insect and mammalian cells, preferably vertebrate cells such as those from a mouse, rat, monkey or human fibroblastic cell line. Yeast host cells include YPH499, YPH500 and YPH501 which are generally available from Stratagene Cloning Systems, La Jolla, Calif. 92037, USA. Preferred mammalian host cells include Chinese hamster ovary (CHO) cells available from the ATCC as CCL61, NIH Swiss mouse embryo cells NIH/3T3 available from the ATCC as CRL 1658, and monkey kidney-derived COS-1 cells available from the ATCC as CRL 1650. Preferred insect cells are Sf9 cells which can be transfected with baculovirus expression vectors.

Transformation of appropriate cell hosts with a DNA construct of the present invention is accomplished by well known methods that typically depend on the type of vector used. With regard to transformation of prokaryotic host cells, see, for example, Cohen et al(1972) *Proc. Natl. Acad Sci. USA* 69, 2110 and Sambrook et al(1989) Molecular Cloning, A Laboratory Manual, Cold Spring Harbor Laboratory, Cold Spring Harbor, N.Y. Transformation of yeast cells is described in Sherman et al(1986) Methods In Yeast Genetics, A Laboratory Manual, Cold Spring Harbor, N.Y. The method of Beggs (1978) *Nature* 275, 104–109 is also useful. With regard to vertebrate cells, reagents useful in transfecting such cells, for example calcium phosphate and DEAE-dextran or liposome formulations, are available from Stratagene Cloning Systems, or Life Technologies Inc., Gaithersburg, Md. 20877, USA.

Electroporation is also useful for transforming and/or transfecting cells and is well known in the art for transforming yeast cell, bacterial cells, insect cells and vertebrate cells.

For example, many bacterial species may be transformed by the methods described in Luchansky et al(1988) *Mol. Microbiol.* 2, 637–646 incorporated herein by reference. The greatest number of transformants is consistently recovered following electroporation of the DNA-cell mixture suspended in 2.5×PEB using 6250V per cm at 25:FD.

Methods for transformation of yeast by electroporation are disclosed in Becker & Guarente (1990) *Methods Enzymol.* 194, 182.

Successfully transformed cells, ie cells that contain a DNA construct of the present invention, can be identified by well known techniques. For example, cells resulting from the introduction of an expression construct of the present invention can be grown to produce the polypeptide of the invention. Cells can be harvested and lysed and their DNA content examined for the presence of the DNA using a method such as that described by Southern (1975) *J. Mol. Biol.* 98, 503 or Berent et al(1985) *Biotech.* 3, 208. Alternatively, the presence of the protein in the supernatant can be detected using antibodies as described below.

In addition to directly assaying for the presence of recombinant DNA, successful transformation can be confirmed by well known immunological methods when the recombinant DNA is capable of directing the expression of the protein. For example, cells successfully transformed with an expression vector produce proteins displaying appropriate antigenicity. Samples of cells suspected of being transformed are harvested and assayed for the protein using suitable antibodies.

Thus, in addition to the transformed host cells themselves, the present invention also contemplates a culture of those cells, preferably a monoclonal (clonally homogeneous) culture, or a culture derived from a monoclonal culture, in a nutrient medium.

A further aspect of the invention provides a method of making the polypeptide of the invention or a variant, derivative, fragment or fusion thereof or a fusion of a variant, fragment or derivative the method comprising culturing a host cell comprising a recombinant polynucleotide or a replicable vector which encodes said polypeptide, and isolating said polypeptide or a variant, derivative, fragment or fusion thereof or a fusion of a variant, fragment or derivative from said host cell. Methods of cultivating host cells and isolating recombinant proteins are well known in the art.

The invention also includes a polypeptide, or a variant, fragment, derivative or fusion thereof, or fusion of a said variant or fragment or derivative obtainable by the above method of the invention.

III. Antibodies

A still further aspect of the invention provides an antibody reactive towards a polypeptide of the invention or a fragment thereof, for example a processed polypeptide of the invention, for example an antibody reactive towards a polypeptide consisting of the amino acid sequence LHAL (SEQ ID NO: 5) or GPIPIRRH (SEQ ID NO: 6). It is particularly useful if the antibodies recognise and bind to an epitope within the amino acid sequences LHAL (SEQ ID NO: 5) and GPIPIRRH (SEQ ID NO: 6).

Antibodies reactive towards the said polypeptide of the invention may be made by methods well known in the art. In particular, the antibodies may be polyclonal or monoclonal.

Suitable monoclonal antibodies which are reactive towards the said polypeptide may be prepared by known techniques, for example those disclosed in "Monoclonal Antibodies: A manual of techniques", H Zola (CRC Press, 1988) and in "Monoclonal Hybridoma Antibodies: Techniques and Applications", S G R Hurrell (CRC Press, 1982).

In a preferred embodiment the antibody is raised using any suitable peptide sequence obtainable from the given amino acid sequence of human NESP55. It is preferred if polyclonal antipeptide antibodies are made. Suitable peptides obtainable from human NESP55 include LHAL (SEQ ID NO: 5; corresponding to residues 172 to 175 of NESP55 and GPIPIRRH (SEQ ID NO: 6; corresponding to residues 247 to 254 of human NESP55). In a preferred embodiment of the invention, an antibody of the invention is capable of preventing or disrupting the interaction between a polypeptide of the invention or a fragment thereof, for example a fragment comprising the amino acid sequence LHAL (SEQ ID NO: 5) or GPIPIRRH (SEQ ID NO: 6) and an interacting polypeptide, for example an interacting polypeptide identified by the method of the invention described below. Such antibodies are believed to be useful in medicine, for example in treating obesity.

It will be appreciated that other antibody-like molecules may be useful in the practice of the invention including, for example, antibody fragments or derivatives which retain their antigen-binding sites, synthetic antibody-like molecules such as single-chain Fv fragments (ScFv) and domain antibodies (dAbs), and other molecules with antibody-like antigen binding motifs. Such antibody-like molecules are included by the term antibody as used herein.

The invention also provides an antibody directed against the peptide sequence GAIPIRRH (SEQ ID NO: 4) for use in medicine and methods of administering such antibodies to treat obesity; the use of such an antibody in the manufacture of a medicament for treating obesity, and a method of treating obesity using such an antibody by administering the antibody to a subject in need of treatment for obesity. Antibodies which recognise the peptide GAIPIRRH (SEQ ID NO: 4) are described in Lovisetti-Scamihorn et al (1999) *Brain Res.* 829, 99–106, but they have not been used to treat obesity.

IV. Peptidomimetics

It will be appreciated that peptidomimetic compounds may also be useful in the practice of the invention. Thus, by "polypeptide" or "peptide" we include not only molecules in which amino acid residues are joined by peptide (—CO—NH—) linkages but also molecules in which the peptide bond is reversed. Such retro-inverso peptidomimetics may be made using methods known in the art, for example such as those described in Meziere et al (1997) *J. Immunol.* 159, 3230–3237, incorporated herein by reference. This approach involves making pseudopeptides containing changes involving the backbone, and not the orientation of side chains. Meziere et al (1997) show that, at least for MHC class II and T helper cell responses, these pseudopeptides are useful. Retro-inverse peptides, which contain NH—CO bonds instead of CO—NH peptide bonds, are much more resistant to proteolysis.

Similarly, the peptide bond may be dispensed with altogether provided that an appropriate linker moiety which retains the spacing between the CI atoms of the amino acid residues is used; it is particularly preferred if the linker moiety has substantially the same charge distribution and substantially the same planarity as a peptide bond.

It will be appreciated that the peptide may conveniently be blocked at its N- or C-terminus so as to help reduce susceptibility to exoproteolytic digestion.

Thus, it will be appreciated that the processed polypeptide, for example which comprises the amino acid sequence LHAL (SEQ ID NO: 5) may be a peptidomimetic compound, as described above. It will be appreciated that the term "polypeptide derivable from" includes the meaning of a peptidomimetic compound corresponding to a polypeptide with an amino acid sequence derived from the amino acid sequence of the said polypeptide.

V. Methods of the Invention

A further aspect of the invention provides human NESP55 for use in medicine and methods of using human NESP55 in medicine, in particular the treatment of obesity. By human NESP55 is included a polypeptide of the invention and human NESP55 as described in Hayward et al (1998) Proc. Nat. Acad. Sci. USA 95:15475–15480 (which lacks the first eight amino acids at the amino terminus of the hNESP55 polypeptide of SEQ ID NO: 2) and variants, fragments, derivatives or fusions or fusions of a variant, fragment or derivative either thereof. Preferences for the said variants, fragments, derivatives or fusions or fusions of a variant, fragment or derivative are as described in the preceding sections. Thus, an embodiment of this aspect of the invention provides a processed polypeptide of the invention for use in medicine and methods of using said processed polypeptide in medicine, in particular in the treatment of obesity. A further embodiment provides a polypeptide consisting of the amino acid sequence LHAL (SEQ ID NO: 5) or GPIPIRRH (SEQ ID NO: 6), or containing the amino acid sequence LHAL (SEQ ID NO: 5) or GPIPIRRH (SEQ ID NO: 6) and flanking sequences as defined above, for use in medicine and methods of using these polypeptides in medicine, in particular the treatment of obesity.

A further aspect of the invention provides a nucleic acid encoding, or complementary to a nucleic acid encoding, human NESP55 or a fragment thereof for use in medicine and methods of using these nucleic acids in medicine, in particular the treatment of obesity. By a nucleic acid encoding human NESP55 is included the nucleic acid encoding human NESP55 described in Hayward et al (1998).

NESP55 or a variant, fragment, derivative or fusion thereof, or a fusion of a variant, fragment or derivative, and peptides containing the amino acid sequences LHAL (SEQ ID NO: 5) and GPIPIRRH (SEQ ID NO: 6) and flanking sequences as defined above are believed to be especially useful in treating obesity. While not being bound by any theory as to why this may be so, we believe that it is due to the involvement of peptides derived from NESP55 in the serotonergic system. Furthermore, as will become clear from the Examples, we have surprisingly shown that NESP55 has a significantly increased level of expression in obese people compared to people with normal weight. Thus, a further aspect of the invention provides a method of treating or preventing obesity in a patient, the method comprising administering to the patient an effective amount of NESP55 as defined above.

A further aspect of the invention provides the use of NESP55 in the manufacture of a medicament for the treatment of obesity. By "NESP55" in the context of the method of treatment and in this aspect of the invention is included human, bovine and mouse NESP55 and a variant, fragment, derivative or fusion, or a fusion of a variant, fragment or derivative of any thereof. Preferences for the said variant, fragment, derivative or fusion or a fusion of a variant, fragment or derivative are equivalent to those indicated above in relation to human NESP55 with the substitution of a reference to bovine or mouse NESP55 for a reference to human NESP55 where appropriate. By human NESP55 is included a polypeptide of the invention and human NESP55 as described in Hayward et al (1998). By mouse and bovine NESP55 are included the mouse and bovine NESP55 sequences reported in Hayward et al (1998). In relation to the treatment and prevention aspects of the invention, NESP55 also includes the processed polypeptides as described above, and the LHAL (SEQ ID NO: 5)-containing, and GPIPIRRH (SEQ ID NO: 6)-containing peptides as described above.

It is preferred that the patient is a human patient. It is further preferred that when the patient is a human patient the NESP55 is human NESP55. or a fragment or variant or derivative or fusion thereof.

An embodiment of this aspect of the invention provides the use of a processed polypeptide of the invention in the manufacture of a medicament for the treatment of obesity. A further embodiment provides the use of a polypeptide consisting of the amino acid sequence LHAL (SEQ ID NO: 5) or LSAL (SEQ ID NO: 3) or GPIPIRRH (SEQ ID NO: 6) or GAIPIRRH (SEQ ID NO: 4) in the manufacture of a medicament for the treatment of obesity. Similarly, these peptides are preferred peptides in the method of treatment or prevention of obesity described above, wherein the peptide is administered to a subject in need of treatment for obesity.

A further aspect of the invention provides a method of identifying a polypeptide (interacting polypeptide) that is capable of interacting with a polypeptide of the invention or a fragment thereof, for example a processed polypeptide of the invention or the LHAL (SEQ ID NO: 5)-containing or GPIPIRRH (SEQ ID NO: 6)-containing polypeptides of the invention, or that is capable of interacting with a polypeptide containing the sequence GAIPIPRRH (SEQ ID NO: 4), the method comprising the steps of (1) exposing the said polypeptide of the invention or fragment thereof, or polypeptide containing the sequence GAIPIPRRH (SEQ ID NO: 4) to a test composition that may comprise a said interacting polypeptide, (2) detecting an interaction between the said polypeptide of the invention or a fragment thereof or polypeptide containing the sequence GAIPIPRRH (SEQ ID NO: 4) and a said interacting polypeptide and optionally (3) identifying and/or isolating the said interacting polypeptide.

Preferably the polypeptide containing the sequence GAIPIRRH (SEQ ID NO: 4) consists of that sequence.

The interaction between the polypeptide of the invention or fragment thereof or the GAIPIRRH (SEQ ID NO: 4)-containing polypeptide and the interacting polypeptide may be measured by any method of detecting/measuring a protein/protein interaction, as discussed further below. Suitable methods include yeast two-hybrid interactions, co-purification, ELISA, co-immunoprecipitation methods and cellular response assays. Cellular response assays may be carried out in adipocytes or adipocyte cell lines, or they may be carried out in adrenal cells, cells of the CNS (including neuronal and glicol cells), epithelial cells (such as gastic cells. The processed polypeptides, such as those containing the sequences LHAL (SEQ ID NO: 5) or GPIPIRRH (SEQ ID NO: 6) or GAIPIRRH (SEQ ID NO: 4) are produced primarily in the adrenal gland and from neurones.

A further method of identifying the interacting polypeptide of the invention includes expression cloning which makes use of the transfection of cDNAs from a cellular source which is believed to encode the interacting polypeptide (such as a receptor) into a suitable cell line (such as a CHO cell line or Hep2A3 cell line) such that at least some of the cell lines express the interacting polypeptide. Cell lines expressing the interacting polypeptide are selected based on the ability of a radiolabelled polypeptide of the invention or GAIPIRRH (SEQ ID NO: 4)-containing peptide to bind to the transfected cell line but not to the non-transfected cell line.

The method may be performed in vitro, either in intact cells or tissues, with broken cell or tissue preparations or at least partially purified components. Alternatively, they may be performed in vivo. The cells tissues or organisms in/on which the method is performed may be transgenic. In particular they may be transgenic for the polypeptide of the invention.

Preferences for the polypeptide of the invention or fragment thereof, for example a processed polypeptide of the invention are as given above. It is particularly preferred that the fragment of the polypeptide of the invention consists of the amino acid sequence LHAL (SEQ ID NO: 5) or GPIPIRRH (SEQ ID NO: 6) or is a LHAL (SEQ ID NO: 5)-containing or GPIPIRRH (SEQ ID NO: 6)-containing polypeptide as described above, and that the interacting polypeptide interacts with these sequences.

Other methods of detecting polypeptide/polypeptide interactions include ultrafiltration with ion spray mass spectroscopy/HPLC methods or other physical and analytical methods. Fluorescence Energy Resonance Transfer (FRET) methods, for example, well known to those skilled in the art, may be used, in which binding of two fluorescent labelled entities may be measured by measuring the interaction of the fluorescent labels when in close proximity to each other.

A further aspect of the invention provides a substantially pure interacting polypeptide identified or identifiable by the method of the invention described above. A still further aspect of the invention provides a nucleic acid encoding the interacting polypeptide of the invention. Methods of identifying the said nucleic acid will be well known to those skilled in the art.

The following methods of isolating a nucleic acid encoding a polypeptide of the invention are given for purposes of illustration and are not considered to be exhaustive.

The polypeptide may be cleaved, for example using trypsin, cyanogen bromide, V8 protease formic acid, or another specific cleavage reagent. The digest may be chromatographed on a Vydac C18 column or subjected to SDS-PAGE to resolve the peptides. The N-terminal sequence of the peptides may then be determined using standard methods.

The sequences are used to isolate a nucleic acid encoding the peptide sequences using standard PCR-based strategies. Degenerate oligonucleotide mixtures, each comprising a mixture of all possible sequences encoding a part of the peptide sequences, are designed and used as PCR primers or probes for hybridisation analysis of PCR products after Southern blotting. mRNA prepared from cells in which the polypeptide may be expressed is used as the template for reverse transcriptase, to prepare cDNA, which is then used as the template for the PCR reactions.

Positive PCR fragments are subcloned and used to screen cDNA libraries to isolate a full length clone for the polypeptide.

Alternatively, the sequences of initial subcloned PCR fragments may be determined, and the sequence may then be extended by known PCR-based techniques to obtain a full length sequence.

Alternatively, the initial PCR sequence may be used to screen electronic databases of expressed sequence tags (ESTs) or other known sequences. By this means, related sequences may be identified which may be useful in isolating a full length sequence using the two approaches described above.

Sequences are determined using the Sanger dideoxy method. The encoded amino acid sequences may be deduced by routine methods.

Techniques used are essentially as described in Sambrook et al (1989) Molecular cloning, a laboratory manual, Cold Spring Harbor Laboratory Press, Cold Spring Harbor, N.Y.

Alternatively, antibodies may be raised against the polypeptide.

The antibodies are used to screen a λgt11 expression library made from cDNA copied from mRNA from cells in which the polypeptide may be expressed.

Positive clones are identified and the insert sequenced by the Sanger method as mentioned above. The encoded amino acid sequence may be deduced by routine methods.

It will be appreciated that it may be desirable to express the polypeptide encoded by the isolated nucleic acid in order to determine that the polypeptide has the expected properties.

The interacting polypeptide may be a receptor molecule, for example a receptor molecule present in/on the surface of a cell, for example an adipocyte or a nerve cell. The receptor molecule may be a transmembrane polypeptide or complex, as know to those skilled in the art.

Less preferably, the interacting polypeptide may be an endoproteolytic processing enzyme. It will be appreciated that known endoproteolytic processing enzymes, for example PC1, PC2 and furin, mentioned above, are not included.

A still further aspect of the invention provides an antagonist of the interacting polypeptide. For example, the antagonist may be an antibody which binds to the interacting polypeptide and blocks the interaction between the interacting polypeptide and the polypeptide of the invention (such as the processed,polypeptides or LHAL (SEQ ID NO: 5)-containing or GPIPIRRH (SEQ ID NO: 6)-containing polypeptides) or the GAIPIRRH (SEQ ID NO: 4)-containing polypeptide.

A further aspect of the invention thus provides a method of identifying a compound capable of disrupting or preventing the interaction between a polypeptide of the invention or a fragment thereof, for example a processed polypeptide of the invention, or a GAIPIRRH (SEQ ID NO: 4)-containing polypeptide and an interacting polypeptide as defined above wherein the polypeptide of the invention or a variant, fragment, derivative or fusion or a fusion of a variant, fragment or derivative thereof, or a GAIPIRRH (SEQ ID NO: 4)-containing polypeptide and/or an interacting polypeptide of the invention are exposed to the said compound and the interaction between the polypeptide of the invention or a variant, fragment, derivative or fusion or a fusion of a variant, fragment or derivative thereof or a GAIPIRRH (SEQ ID NO: 4)-containing polypeptide and an interacting polypeptide of the invention in the presence and absence of the compound is measured.

A further aspect of the invention provides a method of identifying a compound capable of binding to an interacting polypeptide of the invention wherein the ability of the compound to bind to the said interacting polypeptide is measured. The ability of the compound to bind to the said interacting polypeptide may be measured by measuring the ability of the compound to disrupt or prevent the interaction between a polypeptide of the invention or a fragment thereof, for example a processed polypeptide of the invention and an interacting polypeptide, using a method as described above.

The interaction between the polypeptide of the invention or a variant, fragment, derivative or fusion or a fusion of a variant, fragment or derivative thereof or a GAIPIRRH (SEQ ID NO: 4)-containing polypeptide and the interacting polypeptide and its disruption or prevention may be measured by any method of detecting/measuring a protein/protein interaction. Suitable methods include yeast two-hybrid interactions, co-purification, ELISA, co-immunoprecipitation methods and bandshift assays. Further suitable methods may include Scintillation Proximity Assays, as well known to those skilled in the art.

The methods may be performed in vitro, either in intact cells or tissues, with broken cell or tissue preparations or at least partially purified components. Alternatively, they may be performed in vivo. The cells tissues or organisms in/on which the use or methods are performed may be transgenic. In particular they may be transgenic for the polypeptide of the invention or the said interacting protein.

It will be appreciated that screening assays which are capable of high throughput operation will be particularly preferred. Examples may include cell based assays and protein-protein binding assays. An SPA-based (Scintillation Proximity Assay; Amersham International) system may be used. For example, beads comprising scintillant and an interacting polypeptide (which term it will be appreciated includes a polypeptide which capable of interacting with a polypeptide of the invention or fragment thereof and is a fragment of a polypeptide, for example a naturally occuring polypeptide, that is also capable of interacting with a polypeptide of the invention or fragment thereof) may be prepared. The beads may be mixed with a sample comprising, for example, the polypeptide of the invention or fragment thereof, for example a polypeptide comprising the sequence GPIPIRRH (SEQ ID NO: 6) into which a radioactive label has been incorporated and with the test compound. Conveniently this is done in a 96-well format. The plate is then counted using a suitable scintillation counter, using known parameters for the particular radioactive label in an SPA assay. Only the radioactive label that is in proximity to the scintillant, ie only that bound to the polypeptide of the invention or fragment thereof, for example the polypeptide comprising the sequence GPIPIRRH (SEQ ID NO: 6) that is bound to the interacting polypeptide anchored on the beads, is detected. Variants of such an assay, for example in which the interacting polypeptide is immobilised on the scintillant beads via binding to an antibody or antibody fragment, may also be used. It will also be appreciated that the assays may be performed using LHAL (SEQ ID NO: 5)-containing polypeptides and GAIPIRRH (SEQ ID NO: 4)-containing polypeptides.

Without prejudice to the nature of any of the interacting polypeptides of the invention, we believe that at least some may be receptors which signal via cyclic AMP (cAMP). In this case, a preferred assay makes use of a transfected cell which expresses the interacting polypeptide (receptor) and which contains a reporter gene system which contains a cAMP responsive element controlling the expression of the reporter gene. A suitable reporter gene is luciferase. The screening system may be arranged to look for agonists or antagonists.

It will be appreciated that the screening assays of the invention are useful for identifying compounds which may be useful in the treatment of obesity.

The compound may be a drug-like compound or lead compound for the development of a drug-like compound for each of the above methods of identifying a compound. It will be appreciated that the said methods may be useful as screening assays in the development of pharmaceutical compounds or drugs, as well known to those skilled in the art.

The term "drug-like compound" is well known to those skilled in the art, and may include the meaning of a compound that has characteristics that may make it suitable for use in medicine, for example as the active ingredient in a medicament. Thus, for example, a drug-like compound may be a molecule that may be synthesised by the techniques of organic chemistry, less preferably by techniques of molecular biology or biochemistry, and is preferably a small molecule, which may be of less than 5000 daltons molecular weight. A drug-like compound may additionally exhibit features of selective interaction with a particular protein or proteins and be bioavailable and/or able to penetrate cellular membranes, but it will be appreciated that these features are not essential.

The term "lead compound" is similarly well known to those skilled in the art, and may include the meaning that the compound, whilst not itself suitable for use as a drug (for example because it is only weakly potent against its intended target, non-selective in its action, unstable, difficult to synthesise or has poor bioavailability) may provide a starting-point for the design of other compounds that may have more desirable characteristics.

It will be appreciated that the compound may be a polypeptide that is capable of competing with the polypeptide of the invention for binding to the interacting polypeptide. Thus, it will be appreciated that a screening method as described above may be useful in identifying polypeptides that may also interact with the interacting polypeptide, for example a receptor molecule.

It will be understood that it will be desirable to identify compounds that may modulate the activity of the polypeptide(s) in vivo. Thus it will be understood that reagents and conditions used in the method may be chosen such that the interactions between the said polypeptide and the interacting polypeptide are substantially the same as between human NESP55 or a fragment therof and a naturally occuring interacting polypeptide in vivo.

The "drug-like compounds" and "lead compounds" identified in the screening assays of the invention are suitably screened in further screens to determine their potential usefulness in treating obesity. Additional screens which may be carried out include determining the effect of the compounds on food intake, body weight and thermogenesis. This is typically done in rodents.

A further aspect of the invention is a kit of parts useful in carrying out a method, for example a screening method, of the invention. Such a kit may comprise a polypeptide of the invention or a fragment thereof, for example a polypeptide comprising or consisting of the amino acid sequence LHAL (SEQ ID NO: 5) or GPIPIRRH (SEQ ID NO: 6) and an interacting polypeptide, for example a receptor molecule.

A further aspect of the invention provides a compound identified by or identifiable by the screening method of the invention, provided that the compound is not a previously known compound.

It will be appreciated that such a compound may be an inhibitor of the formation or stability of a complex of the polypeptide of the invention or a fragment thereof used in the screen, for example a polypeptide comprising or consisting of the amino acid sequence LHAL (SEQ ID NO: 5) or GPIPIRRH (SEQ ID NO: 6) with an interacting polypeptide(s), for example a receptor, and therefore ultimately a modulator of any activity of that complex, for example any signalling activity, for example protein kinase activity. The intention of the screen may be to identify compounds that act as modulators, for example inhibitors or promoters, preferably inhibitors of the activity of the complex, even if the screen makes use of a binding assay rather than an activity (for example signalling activity) assay. It will be appreciated that the action of a compound found to bind the interacting polypeptide may be confirmed by performing an assay of, for example, protein kinase activity in the presence of the compound. It will be appreciated that a compound that interacts with an interacting polypeptide that is a receptor molecule may act as an agonist or antagonist of any signalling activity of the said receptor.

A further aspect of the invention provides a method of disrupting or preventing the interaction between a polypeptide of the invention or a variant, fragment, derivative or fusion, or a fusion of a variant, fragment or derivative or a fragment thereof, for example a processed polypeptide of the invention and an interacting polypeptide, for example a receptor molecule, as defined above wherein the said interacting polypeptide or polypeptide of the invention or a variant, fragment, derivative or fusion, or a fusion of a variant, fragment or derivative is exposed to a compound of the invention or an antibody of the invention.

Preferences for the polypeptide of the invention and the interacting polypeptide are as set out in relation to earlier aspects of the invention. It is particularly preferred that the polypeptide of the invention or fragment thereof or interacting polypeptide is a naturally occuring polypeptide or naturally occuring allelic variants thereof.

A further aspect of the invention provides a compound identifiable by or identified in a screening assay of the invention for use in medicine and methods of using said compound in medicine, in particular in the treatment of obesity in which the compound is administered to a subject in need of treatment for obesity. A still further aspect of the invention provides an interacting polypeptide of the invention or nucleic acid of the invention or antibody of the invention for use in medicine. A still further aspect of the invention provides a pharmaceutical composition comprising a polypeptide, interacting polypeptide, nucleic acid, antibody and/or compound of the invention and a pharmaceutically acceptable carrier. A suitable carrier will be known to those skilled in the art.

The polypeptide, interacting polypeptide, polynucleotide, compound, antibody, composition or medicament of the invention may be administered in any suitable way, usually parenterally, for example intravenously, intraperitoneally or intravesically, in standard sterile, non-pyrogenic formulations of diluents and carriers. The polypeptide, interacting polypeptide, polynucleotide, compound, antibody, composition or medicament of the invention may also be administered in a localised manner, for example by injection. In general, the compound is administered orally, although this is not preferred for peptides. The compound may be administered intravenously, parenterally or subcutaneously, although these are not preferred.

Without being bound by any theory concerning the human receptor for the LHAL (SEQ ID NO: 5) peptide, and without prejudice to any other aspect of the invention, we believe that the LHAL (SEQ ID NO: 5) peptide interacts with human $5HT_{1B/1D}$ receptors. The molecular cloning and characterization of these receptors is described in Hamblin & Metcalf (1991) Mol. Pharmacol. 40, 143–148 "Primary structure and functional characterization of a human 5-$HT_{1D}$-type serotonin receptor"; Levy et al (1992) J. Biol. Chem. 267, 7553–7662 "Molecular cloning of a human serotonin receptor (S12) with a pharmacological profile resembling that of the 5-$HT_{1D}$ subtype"; and Jin et al (1992) J. Biol. Chem. 267, 5735–5738 "Characterization of the human 5-hydroxytryptamine 1 B receptor"; all of which are incorporated by reference. Using conventional techniques, transfected cells expressing these receptors can be made, and antibodies directed at the receptors can be made in the same way as described above with reference to the interacting polypeptides of the invention.

Thus, a further aspect of the invention provides a method of identifying a compound capable of disrupting or preventing the interaction between the peptide LHAL (SEQ ID NO: 5) and human $5HT_{1B/1D}$ receptor wherein the LHAL (SEQ ID NO: 5)-containing polypeptide and/or the said receptor are exposed to the said compound and the interaction between the polypeptide and the receptor is measured in the presence and absence of the compound.

A still further aspect provides a method of identifying a compound capable of binding to human 5HT$_{1B/1D}$ receptor wherein the ability of the compound to bind to the said interacting polypeptide is measured.

These methods can be carried out using equivalent methods as those described above with reference to the interacting polypeptides of the invention, and the polypeptides of the invention.

A compound identified by or identifiable by the above two methods is part of the invention as is its use in treating or preventing obesity. Similarly, the invention includes the treatment or prevention of obesity using antagonists of human 5-HT$_{1B/1D}$ receptor, such as antibodies reactive with the receptor, and treatment or prevention of obesity using antibodies reactive with the peptide sequence LHAL (SEQ ID NO: 5).

The nucleic acid of the invention may be an antisense oligonucleotide, for example an antisense oligonucleotide directed against a nucleic acid encoding a polypeptide of the invention such as the human NESP55 gene or an interacting polypeptide of the invention which may be a receptor molecule. Antisense oligonucleotides are single-stranded nucleic acid, which can specifically bind to a complementary nucleic acid sequence. By binding to the appropriate target sequence, an RNA-RNA, a DNA-DNA, or RNA-DNA duplex is formed. These nucleic acids are often termed "antisense" because they are complementary to the sense or coding strand of the gene.

Recently, formation of a triple helix has proven possible where the oligonucleotide is bound to a DNA duplex. It was found that oligonucleotides could recognise sequences in the major groove of the DNA double helix. A triple helix was formed thereby. This suggests that it is possible to synthesise a sequence-specific molecules which specifically bind double-stranded DNA via recognition of major groove hydrogen binding sites.

By binding to the target nucleic acid, the above oligonucleotides can inhibit the function of the target nucleic acid. This could, for example, be a result of blocking the transcription, processing, poly(A)addition, replication, translation, or promoting inhibitory mechanisms of the cells, such as promoting RNA degradations.

Antisense oligonucleotides are prepared in the laboratory and then introduced into cells, for example by microinjection or uptake from the cell culture medium into the cells, or they are expressed in cells after transfection with plasmids or retroviruses or other vectors carrying an antisense gene. Antisense oligonucleotides were first discovered to inhibit viral replication or expression in cell culture for Rous sarcoma virus, vesicular stomatitis virus, herpes simplex virus type 1, simian virus and influenza virus. Since then, inhibition of mRNA translation by antisense oligonucleotides has been studied extensively in cell-free systems including rabbit reticulocyte lysates and wheat germ extracts. Inhibition of viral function by antisense oligonucleotides has been demonstrated in vitro using oligonucleotides which were complementary to the AIDS HIV retrovirus RNA (Goodchild, J. 1988 "Inhibition of Human Immunodeficiency Virus Replication by Antisense Oligodeoxynucleotides", *Proc. Natl. Acad. Sci. (USA)* 85(15), 5507–11). The Goodchild study showed that oligonucleotides that were most effective were complementary to the poly(A) signal; also effective were those targeted at the 5N end of the RNA, particularly the cap and 5N untranslated region, next to the primer binding site and at the primer binding site. The cap, 5N untranslated region, and poly(A) signal lie within the sequence repeated at the ends of retrovirus RNA (R region) and the oligonucleotides complementary to these may bind twice to the RNA.

Oligonucleotides are subject to being degraded or inactivated by cellular endogenous nucleases. To counter this problem, it is possible to use modified oligonucleotides, eg having altered internucleotide linkages, in which the naturally occurring phosphodiester linkages have been replaced with another linkage. For example, Agrawal et al (1988) *Proc. Natl. Acad. Sci. USA* 85, 7079–7083 showed increased inhibition in tissue culture of HIV-1 using oligonucleotide phosphoramidates and phosphorothioates. Sarin et al (1988) *Proc. Natl. Acad Sci. USA* 85, 7448–7451 demonstrated increased inhibition of HIV-1 using oligonucleotide methylphosphonates. Agrawal et al (1989) *Proc. Natl. Acad. Sci. USA* 86, 7790–7794 showed inhibition of HIV-1 replication in both early-infected and chronically infected cell cultures, using nucleotide sequence-specific oligonucleotide phosphorothioates. Leither et al (1990) *Proc. Natl. Acad Sci. USA* 87, 3430–3434 report inhibition in tissue culture of influenza virus replication by oligonucleotide phosphorothioates.

Oligonucleotides having artificial linkages have been shown to be resistant to degradation in vivo. For example, Shaw et al (1991) in *Nucleic Acids Res.* 19, 747–750, report that otherwise unmodified oligonucleotides become more resistant to nucleases in vivo when they are blocked at the 3☐ end by certain capping structures and that uncapped oligonucleotide phosphorothioates are not degraded in vivo.

A detailed description of the H-phosphonate approach to synthesising oligonucleoside phosphorothioates is provided in Agrawal and Tang (1990) *Tetrahedron Letters* 31, 7541–7544, the teachings of which are hereby incorporated herein by reference. Syntheses of oligonucleoside methylphosphonates, phosphorodithioates, phosphoramidates, phosphate esters, bridged phosphoramidates and bridge phosphorothioates are known in the art. See, for example, Agrawal and Goodchild (1987) *Tetrahedron Letters* 28, 3539; Nielsen et al (1988) *Tetrahedron Letters* 29, 2911; Jager et al (1988) *Biochemistry* 27, 7237; Uznanski et al (1987) *Tetrahedron Letters* 28, 3401; Bannwarth (1988) *Helv. Chim. Acta.* 71, 1517; Crosstick and Vyle (1989) *Tetrahedron Letters* 30, 4693; Agrawal et al (1990) *Proc. Natl. Acad. Sci. USA* 87, 1401–1405, the teachings of which are incorporated herein by reference. Other methods for synthesis or production also are possible. In a preferred embodiment the oligonucleotide is a deoxyribonucleic acid (DNA), although ribonucleic acid (RNA) sequences may also be synthesised and applied.

The oligonucleotides useful in the invention preferably are designed to resist degradation by endogenous nucleolytic enzymes. In vivo degradation of oligonucleotides produces oligonucleotide breakdown products of reduced length. Such breakdown products are more likely to engage in non-specific hybridization and are less likely to be effective, relative to their full-length counterparts. Thus, it is desirable to use oligonucleotides that are resistant to degradation in the body and which are able to reach the targeted cells. The present oligonucleotides can be rendered more resistant to degradation in vivo by substituting one or more internal artificial internucleotide linkages for the native phosphodiester linkages, for example, by replacing phosphate with sulphur in the linkage. Examples of linkages that may be used include phosphorothioates, methylphosphonates, sulphone, sulphate, ketyl, phosphorodithioates, various phosphoramidates, phosphate esters, bridged phosphorothioates and bridged phosphoramidates. Such examples are illustrative, rather than limiting, since other internucleotide linkages are known in the art. See, for example, Cohen, (1990) *Trends in Biotechnology*. The synthesis of oligonucleotides having one or more of these linkages substituted for the phosphodiester internucleotide linkages is well known in the art, including synthetic pathways for producing oligonucleotides having mixed internucleotide linkages.

Oligonucleotides can be made resistant to extension by endogenous enzymes by "capping" or incorporating similar groups on the 5' or 3' terminal nucleotides. A reagent for capping is commercially available as Amino-LinkII™ from Applied BioSystems Inc, Foster City, Calif. Methods for capping are described, for example, by Shaw et al (1991) *Nucleic Acids Res.* 19, 747–750 and Agrawal et al (1991) *Proc. Natl. Acad. Sci. USA* 88(17), 7595–7599, the teachings of which are hereby incorporated herein by reference.

A further method of making oligonucleotides resistant to nuclease attack is for them to be "self-stabilised" as described by Tang et al (1993) *Nucl. Acids Res.* 21, 2729–2735 incorporated herein by reference. Self-stabilised oligonucleotides have hairpin loop structures at their 3' ends, and show increased resistance to degradation by snake venom phosphodiesterase, DNA polymerase I and fetal bovine serum. The self-stabilised region of the oligonucleotide does not interfere in hybridization with complementary nucleic acids, and pharmacokinetic and stability studies in mice have shown increased in vivo persistence of self-stabilised oligonucleotides with respect to their linear counterparts.

It will be appreciated that antisense agents also include larger molecules which bind to said interacting polypeptide mRNA or genes and substantially prevent expression of said interacting polypeptide mRNA or genes and substantially prevent expression of said interacting polypeptide. Thus, expression of an antisense molecule which is substantially complementary to said interacting polypeptide is envisaged as part of the invention.

The said larger molecules may be expressed from any suitable genetic construct as is described below and delivered to the patient. Typically, the genetic construct which expresses the antisense molecule comprises at least a portion of the said interacting polypeptide coding sequence operatively linked to a promoter which can express the antisense molecule in the cell. Suitable promoters will be known to those skilled in the art, and may include promoters for ubiquitously expressed, for example housekeeping genes or for tissue-specific genes, depending upon where it is desired to express the antisense molecule.

Although the genetic construct can be DNA or RNA it is preferred if it is DNA.

Preferably, the genetic construct is adapted for delivery to a human cell.

Means and methods of introducing a genetic construct into a cell in an animal body are known in the art. For example, the constructs of the invention may be introduced into the cells by any convenient method, for example methods involving retroviruses, so that the construct is inserted into the genome of the (dividing) cell.

Other methods involve simple delivery of the construct into the cell for expression therein either for a limited time or, following integration into the genome, for a longer time. An example of the latter approach includes liposomes (Nassander et al (1992) *Cancer Res.* 52, 646–653). Other methods of delivery include adenoviruses carrying external DNA via an antibody-polylysine bridge (see Curiel *Prog. Med. Virol.* 40, 1–18) and transferrin-polycation conjugates as carriers (Wagner et al (1990) *Proc. Natl. Acad Sci. USA* 87, 3410–3414). The DNA may also be delivered by adenovirus wherein it is present within the adenovirus particle. It will be appreciated that "naked DNA" and DNA complexed with cationic and neutral lipids may also be useful in introducing the DNA of the invention into cells of the patient to be treated. Non-viral approaches to gene therapy are described in Ledley (1995) *Human Gene Therapy* 6, 1129–1144. Alternative targeted delivery systems are also known such as the modified adenovirus system described in WO 94/10323 wherein, typically, the DNA is carried within the adenovirus, or adenovirus-like, particle. Michael et al (1995) *Gene Therapy* 2, 660–668 describes modification of adenovirus to add a cell-selective moiety into a fibre protein. Mutant adenoviruses which replicate selectively in p53-deficient human tumour cells, such as those described in Bischoff et al (1996) *Science* 274, 373–376 are also useful for delivering the genetic construct of the invention to a cell. Thus, it will be appreciated that a further aspect of the invention provides a virus or virus-like particle comprising a genetic construct of the invention. Other suitable viruses or virus-like particles include HSV, AAV, vaccinia and parvovirus.

A ribozyme capable of cleaving the interacting polypeptide RNA or DNA. A gene expressing said ribozyme may be administered in substantially the same and using substantially the same vehicles as for the antisense molecules. Ribozymes which may be encoded in the genomes of the viruses or virus-like particles herein disclosed are described in Cech and Herschlag "Site-specific cleavage of single stranded DNA" U.S. Pat. No. 5,180,818; Altman et al "Cleavage of targeted RNA by RNAse P" U.S. Pat. No. 5,168,053, Cantin el al "Ribozyme cleavage of HIV-1 RNA" U.S. Pat. No. 5,149,796; Cech et al "RNA ribozyme restriction endoribonucleases and methods", U.S. Pat. No. 5,116,742; Been et al "RNA ribozyme polymerases, dephosphorylases, restriction endonucleases and methods", U.S. Pat. No. 5,093,246; and Been et al "RNA ribozyme polymerases, dephosphorylases, restriction endoribonucleases and methods; cleaves single-stranded RNA at specific site by transesterification", U.S. Pat. No. 4,987,071, all incorporated herein by reference.

The genetic constructs of the invention can be prepared using methods well known in the art.

A further aspect of the invention provides a method of determining whether an to individual is likely to become or remain obese or become more obese comprising determining the level of NESP55 or a fragment derived or derivable from NESP55 or determining the level of a messenger RNA encoding NESP55 in a tissue sample, or determining the level of activity of NESP55 in a tissue sample, for example a body fluid, and determining that the said level differs from a level found in an individual that is not obese and/or not expected to become obese. The patient may be a patient that is obese (as judged, for example, by Body Mass Index) or a patient at risk of obesity, for example as judged on the basis of a family history of obesity or on a history or family history of conditions associated with or leading to obesity.

The level of expression of NESP55 itself can usefully be measured or the level of a fragment which is derived, or is derivable, from NESP55 may usefully be measured.

The invention also provides kits of parts for carrying out the method of determining whether an individual is likely to become or remain obese or become more obese. The kit of parts contains any means for determining the level of NESP55 or a fragment derived or derivable from NESP55 or any means for determining the level of a messenger RNA encoding NESP55. Thus, the kit may contain antibodies directed against NESP55 or a fragment thereof and other components required to carry out, for example, an ELISA test. The kit may contain oligonucleotide primers and other suitable reagents for carrying out a PCR-based analysis of NESP55 mRNA.

A further aspect of the invention provides the use of an inhibitor of a polypeptide that is capable of cleaving NESP55 in the manufacture of a medicament for treating obesity. It is preferred that the said polypeptide is not capable of cleaving chromogranin A or chromogranin B and that the said inhibitor is not capable of inhibiting the cleavage of chromogranin A or chromogranin B.

A further aspect of the invention provides a compound capable of altering the expression of NESP55. The said compound may be an antisense molecule or ribozyme directed (for example, capable of binding to a polynucleotide encoding NESP55 under physiological conditions) against a polynucleotide encoding NESP55. A further aspect of the invention provides a compound capable of altering the expression of NESP55 for use in medicine. A still further aspect of the invention provides the use of a compound capable of altering the expression of NESP55 in the manufacture of a medicament for the treatment of obesity.

The invention will now be described in detail with reference to the following Examples and Figures wherein:

FIG. 1 shows a comparison between the human NESP55 amino acid sequence (hNESP55) and bovine NESP55 (bNESP55).

EXAMPLE 1

An Increased Level of NESP55 Expression is Associated With Obesity

We have undertaken a sophisticated search of a database which has identified a gene, hNESP55, which has a significantly increased level of expression in obese donors when compared to donors of normal weight. The procedure used a database of sequence and expression data to compare (a) the expression levels of genes in tissues from donors with a desirable weight, ie with a Body Mass Index (BMI) value between 20 and 25 with (b) the expression levels of genes in tissues from obese and severely obese donors, ie with a BMI value greater than 30.

The database used is a database of human gene sequence and expression for hundreds of different tissues and cells in both normal and diseased systems and at different developmental stages (eg embryonic, fetal and adult tissue). It currently contains over 3 million ESTs. The ESTs are cDNA clones derived from mRNA from various tissues and from various donors. Libraries of ESTs have been established in respect of different donors.

The BMI for the various donors has been calculated and the pooled tissues from obese and severely obese donors was subsequently compared with pooled tissues from desirable weight donors. The database which contained 267 donors with both height and weight entries, who had contributed 302 tissue libraries.

A crude search was undertaken to determine what genes are expressed in tissues from severely obese donors and not in tissues from desirable weight donors. A more rigorous search compared the libraries from donors with desirable weights (BMI between 20 and 25) with libraries from obese and severely obese donors (BMI greater than 30) to determine which genes were over/under-expressed.

An EST was identified using these procedures which has homology to the bovine gene coding for neuroendocrine secretory protein 55 (NESP55).

An EST clone was obtained and sequenced. The predicted amino acid sequence is shown in SEQ ID NO: 2 and in FIG. 1 compared to the bovine NESP55 sequence, and the nucleotide sequence is shown in SEQ ID NO: 1. The cDNA appears to be full-length and has an open reading frame of 253 amino acids. The overall homology between the human and bovine sequences is 84%, strongly suggesting that it is a functional homologue of NESP55. We have called the protein human NESP55 (hNESP55). The neuropeptide 5-HT Moduline sequence, encoded by residues 170 to 180 of the full sequence, contains one amino acid change: instead of the sequence LSAL (SEQ ID NO: 3), the sequence has LHAL (SEQ ID NO: 5): compare QRLHALKLRSP (SEQ ID NO: 13; residues 170 to 180 of hNESP55 in FIG. 1) and ERLSALRLRSP (SEQ ID NO: 14; residues 170 to 180 of bNESP55 in FIG. 1).

A second bioactive peptide has been identified within the amino acid sequence of the bovine NESP55 protein. The peptide GAIPIRRH (SEQ ID NO: 4) has been found in chromaffin granules but no function has been assigned. The equivalent peptide from hNESP55 has the amino acid sequence GPIPIRRH (SEQ ID NO: 6). The amino acids flanking both bioactive peptides are different. Since these are the sites of endoproteolytic cleavage necessary to produce the peptides, this may represent species variability in recognition sequences; however, conservation of charge may be sufficient.

In contrast to the situation in the bovine situation, hNESP55 could only be detected in libraries extracted from the endocrine system. Expression could not be detected in any other tissue category, notably including nervous and cardiovascular. The EST clone identified from the library was from an adrenal tumour library isolated from a 57 year old female with a BMI of 36.

EXAMPLE 2

Screening Assay

A CHO cell is transfected with the human receptor for the peptide GPIPIRRH (SEQ ID NO: 6) which is expressed on the cell surface. Radiolabelled GPIPIRRH (SEQ ID NO: 6) is incubated with the transfected cell and binds to the receptor. Compounds are tested to determine whether they specifically displace the GPIPIRRH (SEQ ID NO: 6) peptide from the cell surface. Compounds that do are selected for further study.

What is claimed is:

1. An isolated polypeptide comprising an amino acid sequence, which is at least 98% identical to the amino acid sequence of SEQ ID NO: 2.

2. The isolated polypeptide of claim 1, which is at least 99.5% identical to the amino acid sequence of SEQ ID NO: 2.

3. An isolated peptide consisting of the amino acid sequence LHAL (SEQ ID NO: 5).

4. An isolated peptide consisting of the amino acid sequence GPIPIRRH (SEQ ID NO: 6).

5. A composition comprising the polypeptide of claim 3 and a pharmaceutically acceptable carrier.

6. A composition comprising the polypeptide of claim 4 and a pharmaceutically acceptable carrier.

* * * * *